(12) United States Patent
Guo et al.

(10) Patent No.: US 9,157,856 B2
(45) Date of Patent: Oct. 13, 2015

(54) INTEGRATED PHOTONIC CRYSTAL STRUCTURES AND THEIR APPLICATIONS

(71) Applicants: Yunbo Guo, San Antonio, TX (US); Harish Subbaraman, Austin, TX (US); Ray T. Chen, Austin, TX (US)

(72) Inventors: Yunbo Guo, San Antonio, TX (US); Harish Subbaraman, Austin, TX (US); Ray T. Chen, Austin, TX (US)

(*) Notice: Subject to any disclaimer, the term of this patent is extended or adjusted under 35 U.S.C. 154(b) by 130 days.

(21) Appl. No.: 14/022,925

(22) Filed: Sep. 10, 2013

(65) Prior Publication Data
US 2014/0070082 A1 Mar. 13, 2014

Related U.S. Application Data

(60) Provisional application No. 61/699,042, filed on Sep. 10, 2012.

(51) Int. Cl.
G01N 21/59 (2006.01)
G02F 1/11 (2006.01)
G02F 1/17 (2006.01)

(52) U.S. Cl.
CPC .............. *G01N 21/59* (2013.01); *G02F 1/17* (2013.01); *G02F 1/11* (2013.01); *G02F 2202/12* (2013.01); *G02F 2202/32* (2013.01)

(58) Field of Classification Search
CPC ................................ G01N 21/59; G02F 1/11
See application file for complete search history.

(56) References Cited

U.S. PATENT DOCUMENTS

| 5,898,517 | A  | * | 4/1999  | Weis ........................ 356/5.09 |
| 7,639,362 | B2 |   | 12/2009 | Ye et al. |
| 2004/0150873 | A1 | * | 8/2004 | Pearsall .................... 359/321 |
| 2004/0179803 | A1 | * | 9/2004 | Bourelle .................... 385/129 |
| 2008/0225293 | A1 | * | 9/2008 | Ye et al. .................... 356/364 |
| 2011/0001063 | A1 | * | 1/2011 | Barker et al. ............. 250/493.1 |
| 2013/0168536 | A1 |   | 7/2013 | Guo et al. |
| 2013/0235441 | A1 | * | 9/2013 | Davis et al. .............. 359/204.4 |

* cited by examiner

*Primary Examiner* — Charlie Y Peng

(57) ABSTRACT

Devices, methods and systems based on integrated photonic crystal structures are disclosed. An integrated photonic crystal structure includes a photonic crystal structure and a defect member disposed adjacent the photonic crystal structure. The defect member includes a photoconductive material. The integrated photonic crystal structure is configured to receive an input light signal such that the input light signal is internally reflected within the photonic crystal structure and the defect member, such that the input light signal is absorbed by the photoconductive material in the defect member, and such that a property of the photoconductive material is changed to thereby output an output signal.

20 Claims, 18 Drawing Sheets

INTEGRATED PHOTONIC CRYSTAL STRUCTURES AND THEIR APPLICATIONS

CROSS-REFERENCE TO RELATED APPLICATION

This application claims priority under 35 U.S.C. §119(e) to the Provisional Patent U.S. Application Ser. No. 61/699,042 entitled "INTEGRATED PHOTONIC CRYSTAL STRUCTURES AND THEIR APPLICATIONS," filed on Sep. 10, 2012, which is incorporated by reference herein in its entirety.

TECHNICAL FIELD

The present disclosure relates to photonic crystal and, more specifically, relates to photoconductive material integrated photonic crystal structures and various applications of the same.

BACKGROUND

Photonic crystals (PCs) have become attractive optical materials for controlling and manipulating the flow of light. PCs are composed of periodic dielectric or metallic-dielectric structures in one-dimensional (1D), two-dimensional (2D), or three-dimensional (3D) directions, and affect the propagation of electromagnetic waves by defining allowed and forbidden photonic bands. The perfect photonic crystal is quite elegant and beautiful, but it becomes even more useful when a desired defect is introduced into the regular crystal structure. A photon-localized state can be created in the photonic band gap due to a structural defect in the PCs, and the electrical field around the defect can be confined and enhanced. If special materials are contained in the defect, PC structures can be developed as functional photonic devices. Selection from various types of PCs depends on specific applications.

In some cases of controlling light beams which are close to plane waves, a 1D PC (i.e., multilayer structure) is sufficient and preferable due to its simplicity in fabrication. 1D PCs have been used in various applications, such as low-threshold lasers, photodiodes and photodetectors, and optical biosensors. However, in some applications, an additional or separate light detector is required to measure a reflected light signal or an emitted signal, which makes 1D PC based systems complicated and hard to realize compact and integrated systems.

SUMMARY

In one general implementation, a device includes a photonic crystal structure and a defect member disposed adjacent the photonic crystal structure. The defect member includes a photoconductive material. The device is configured to receive the input light signal such that the input light signal is internally reflected within the photonic crystal structure and the defect member, such that the input light signal is absorbed by the photoconductive material in the defect member, and such that a property of the photoconductive material is changed to thereby output an output signal.

In another general implementation, a method includes providing a photoconductive material incorporated in a defect member disposed adjacent a photonic crystal structure, and emitting an input light signal to the photonic crystal structure such that the input light signal is internally reflected within the photonic crystal structure and the defect member, such that the input light signal is absorbed by the photoconductive material in the defect member, and such that a property of the photoconductive material is changed to thereby output an output signal.

In a third general implementation, a system including a plurality of devices is disclosed. Each device includes a photonic crystal structure and a defect member disposed adjacent the photonic crystal structure. The defect member includes a photoconductive material. The device is configured to receive an input light signal such that the input light signal is internally reflected within the photonic crystal structure and the defect member, such that the input light signal is absorbed by the photoconductive material in the defect member, and such that a property of the photoconductive material is changed.

Implementations can optionally include one or more of the following features in the device. In certain aspects of the device, the photoconductive material can include one or more of silicon, germanium, InGaAs, PbS, PbSe, GaAs, and graphene. The structure of the photoconductive material can include amorphous, polycrystalline, crystalline, monolayer, p-n, or p-i-n. The property of the photoconductive material can include electrical conductivity, and the output signal includes one or more of a current, a resistance, and a voltage. The input light signal can include light from at least one of a light source and an object. The light signal can include s-polarization light or p-polarization light.

In some particular aspects, the defect member can define an exposed operative surface and the output signal is associated with a condition at the operative surface. The condition at the operative surface can be detected by detecting a change in the output signal. The operative surface can be on one side of the defect member opposite to that of the photonic crystal structure so as to be exposed to an external influence that alters the condition at the operative surface. The external influence that affects the condition at the operative surface can be determined by measuring the output signal. The external influence can include one or more of an acoustic input, an ultrasound input, a pressure input, a change of ambient medium, and material adsorbed on the operative surface. The defect member can include one of an elastic material, a semi-rigid material, and a rigid material. A thickness of the defect member can be determined by the resonant condition in the defect member.

In certain aspects, the device can further include a light coupler between the input light signal and the photonic crystal structure. The input light signal can be inputted to the photonic crystal structure via the light coupler. The light coupler can be configured to change the incident angle of the input light signal such that the input light signal is internally reflected within the photonic crystal structure and the defect member, and the light coupler can include at least one of a grating, a reflector, and a prism. The device can further include a substrate. The light coupler can be interposed between the substrate and the photonic crystal structure, and the substrate can be one of a flexible substrate, a semi-rigid substrate, and a rigid substrate.

In particular aspects, the device can include a light source for providing the input light signal. The light source can be interposed between the substrate and the light coupler. A change of the input light signal can be determined by measuring the change of the output signal, and the change of the input light signal can include one or more of an intensity change, a wavelength change, and a polarization change. In certain cases, the photoconductive material is an active gain medium, and the output signal is an excited laser signal. The device can be configured to be one of a photodetector, a photoresistor, an acoustic sensor, an ultrasonic sensor, a pressure sensor, and a biosensor.

Implementations can optionally include one or more of the following features in the method. In certain implementations, the method can include providing a light coupler between the input light signal and the photonic crystal structure such that the input light signal is internally reflected within the photonic crystal structure and the defect member. The method can include providing an exposed operative surface defined by the defect member, and detecting the output signal to thereby detect an external influence on the operative surface.

In particular aspects, the method can include providing an elastic material incorporated in the defect member; and detecting the output signal to thereby detect flexure of the elastic material due to the external influence, the external influence including at least one of a pressure input, an acoustic input, and an ultrasonic input.

In another particular aspects, the method can include providing a dielectric material incorporated in the defect member, and detecting the output signal to thereby detect the external influence, the external influence including at least one of material adsorbed on the operative surface or a change of ambient medium on the operative surface.

Implementations can optionally include one or more of the following features in the system. In certain aspects of the system, the system can include application specific integrated circuits coupled to the plurality of devices. The application specific integrated circuits can be configured to receive the output signals. The system can further include data acquisition and analysis systems coupled to the application specific integrated circuits. The data acquisition and analysis system can be configured to process the output signals. In particular aspects, the plurality of devices are configured into arrays to thereby operate as a multiplexing system, the multiplexing system being one of a photodetector array, an acoustic sensor array, an ultrasonic sensor array, a pressure sensor array, and a biosensor array.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure in any way.

Figure 1:
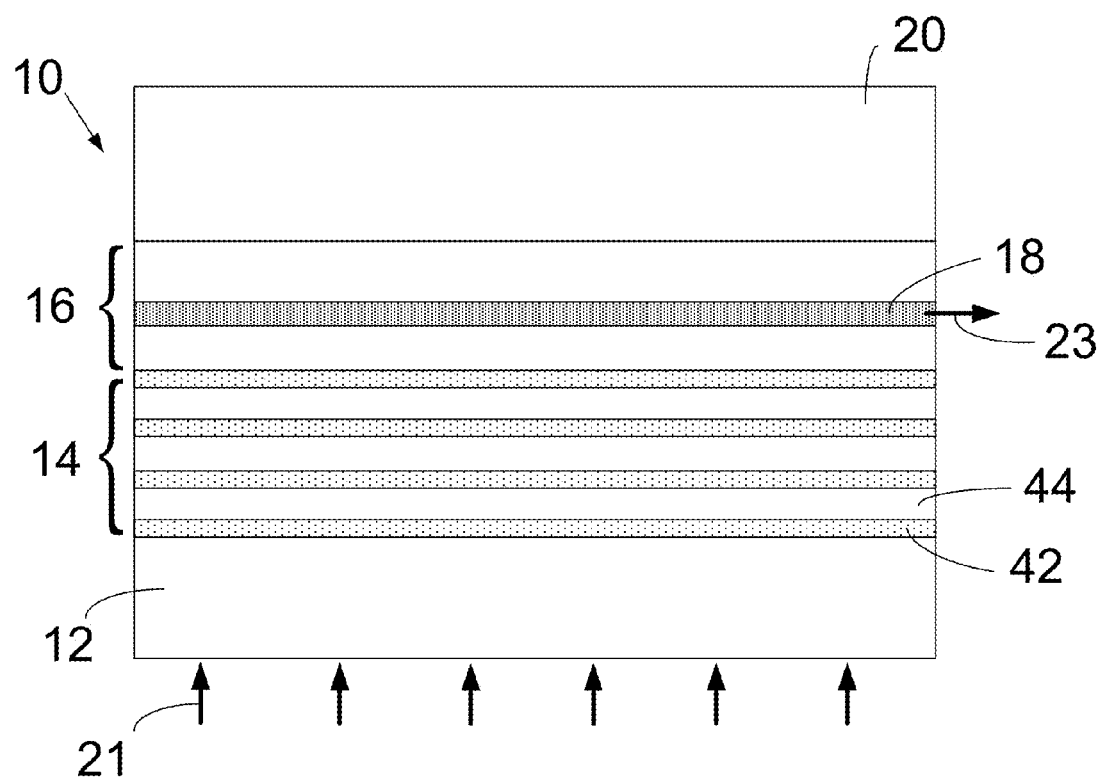
FIG. 1 is a schematic view of an integrated photonic crystal (IPC) structure, according to various exemplary embodiments of the present disclosure.
Figure 2A:
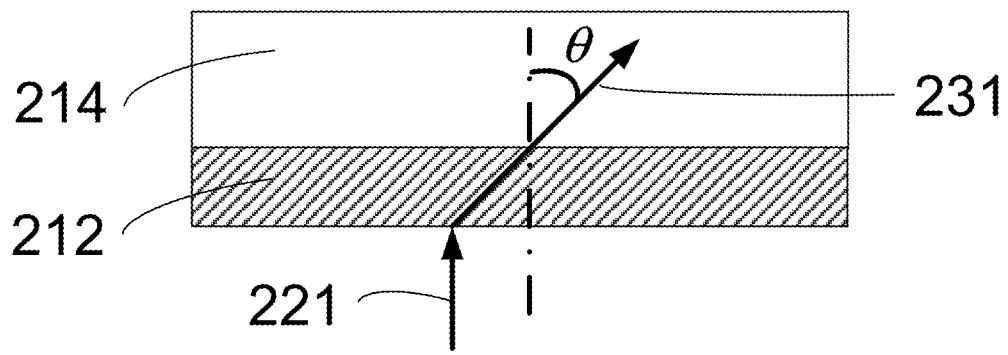
FIGS. 2A-2C are schematic views of a light coupler configuration of the IPC structure of FIG. 1 according to additional embodiments of the present disclosure, including: grating coupler (FIG. 2A), reflector coupler (FIG. 2B), and prism coupler (FIG. 2C).
Figure 2B:
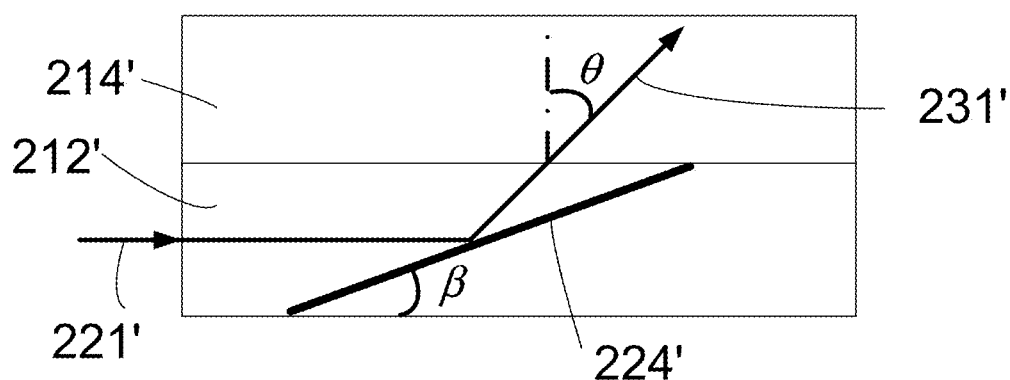
Figure 2C:
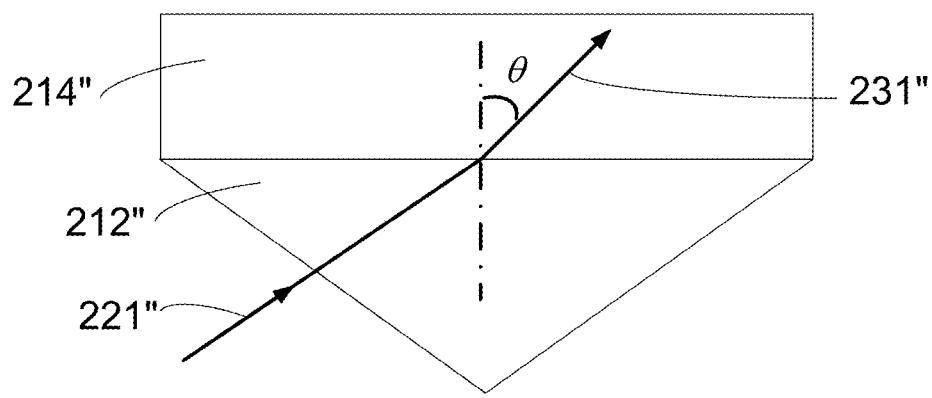
Figure 16A:
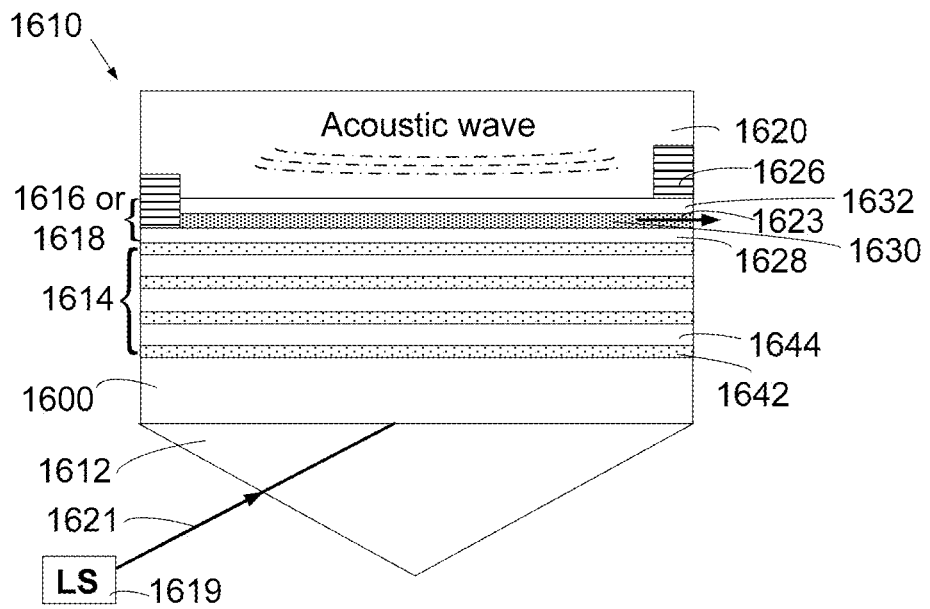
Figure 16B:
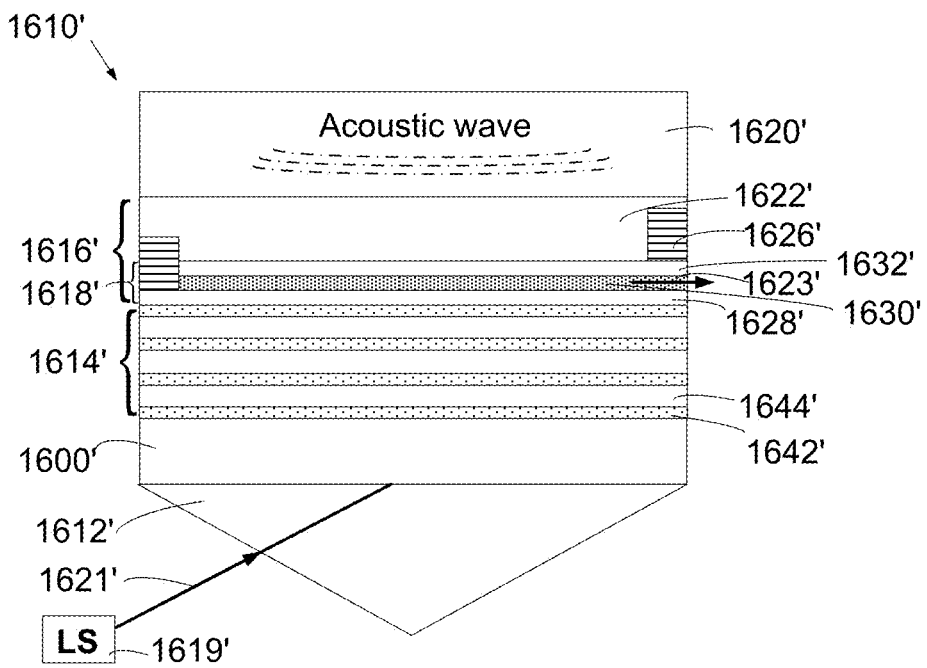
Figure 16C:
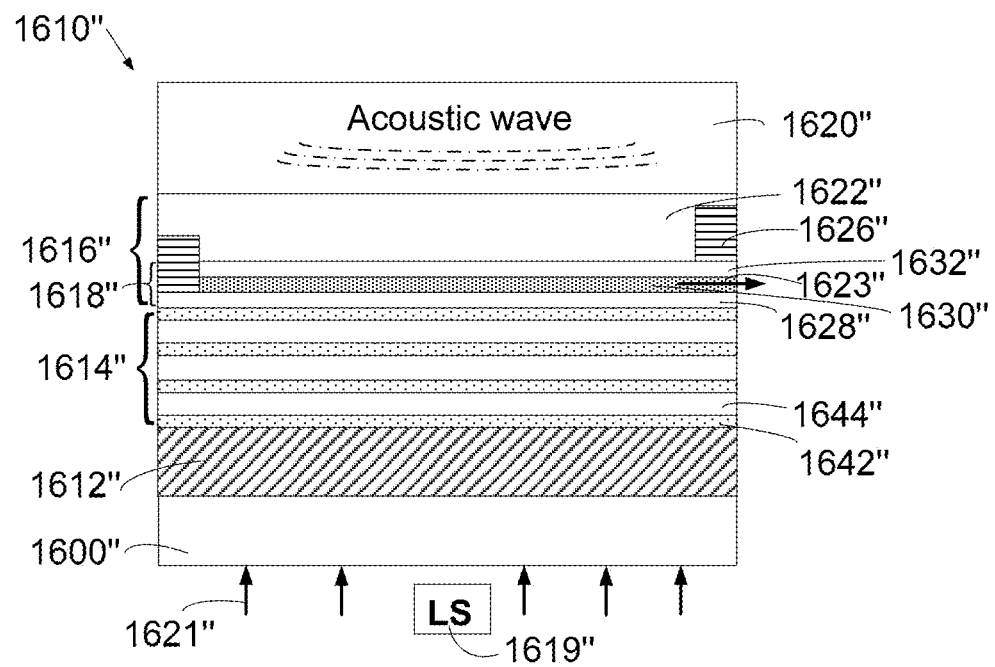

FIG. 16A is the schematic of the IPC structure of FIG. 1 for a PC-based photodetector with a prism coupler, as illustrated in FIG. 2C; FIG. 16B is the schematic of the IPC structure of FIG. 1 for an optical acoustic sensor with a prism coupler, as illustrated in FIG. 2C; FIG. 16C is the schematic of the IPC structure of FIG. 1 for an integrated optical acoustic sensor with a grating coupler illustrated in FIG. 2A.

Figure 17:
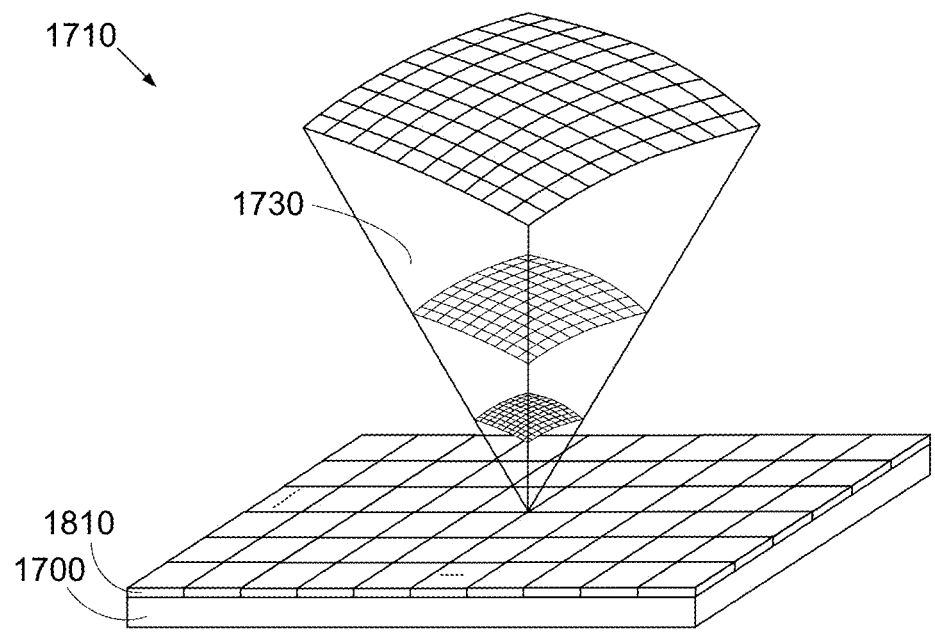

FIG. 17 is the schematic of the IPC structure of FIG. 1 for an integrated optical ultrasound transducer array for ultrasound imaging according to additional embodiments of the present disclosure.

Figure 18:
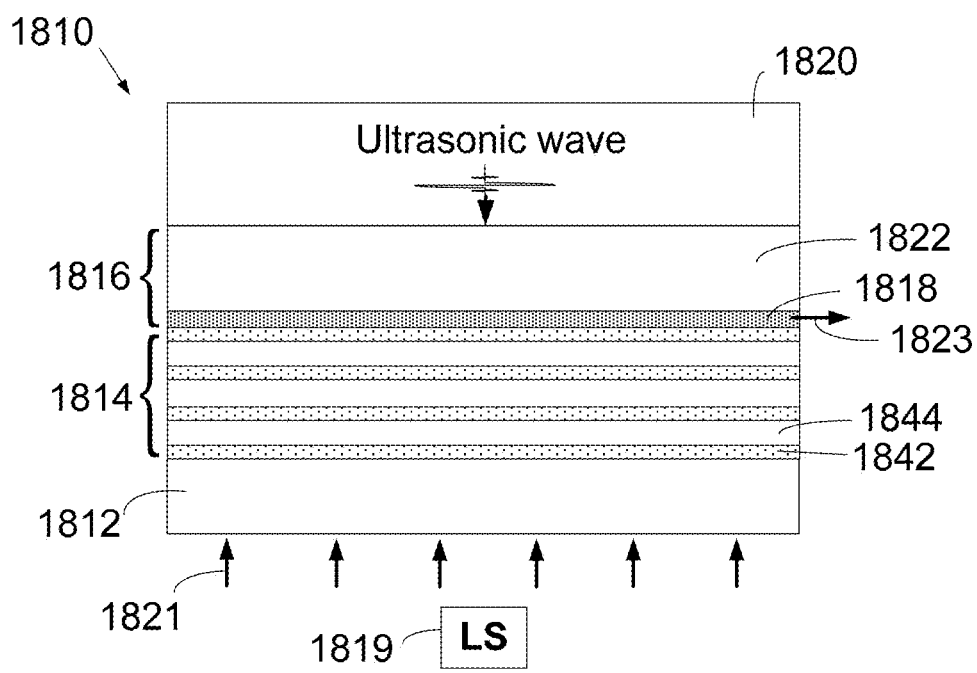

FIG. 18 is the schematic of the IPC structure of FIG. 1 for an integrated optical ultrasound transducer according to additional embodiments of the present disclosure.

Figure 19:
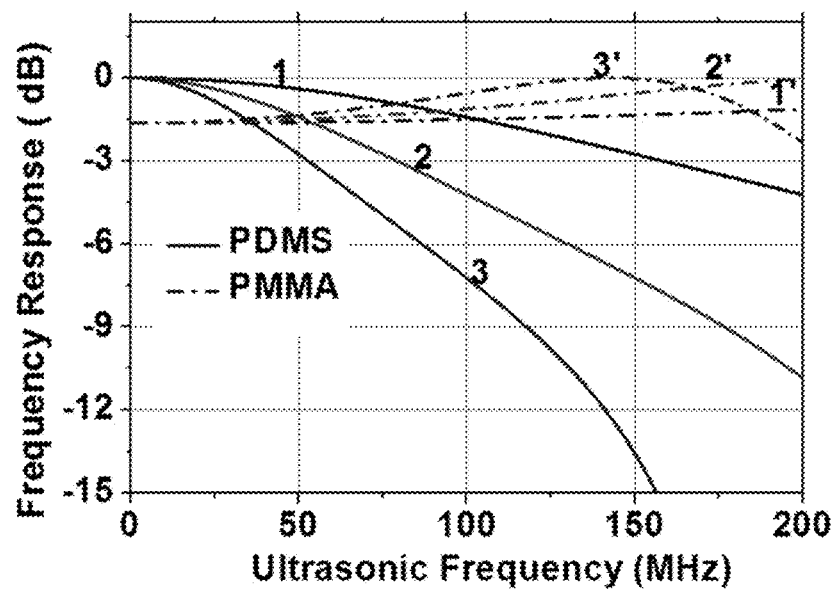

FIG. 19 is the simulated frequency response of the IPC structure of FIG. 1 for an integrated optical ultrasound transducer.

Figure 20A:
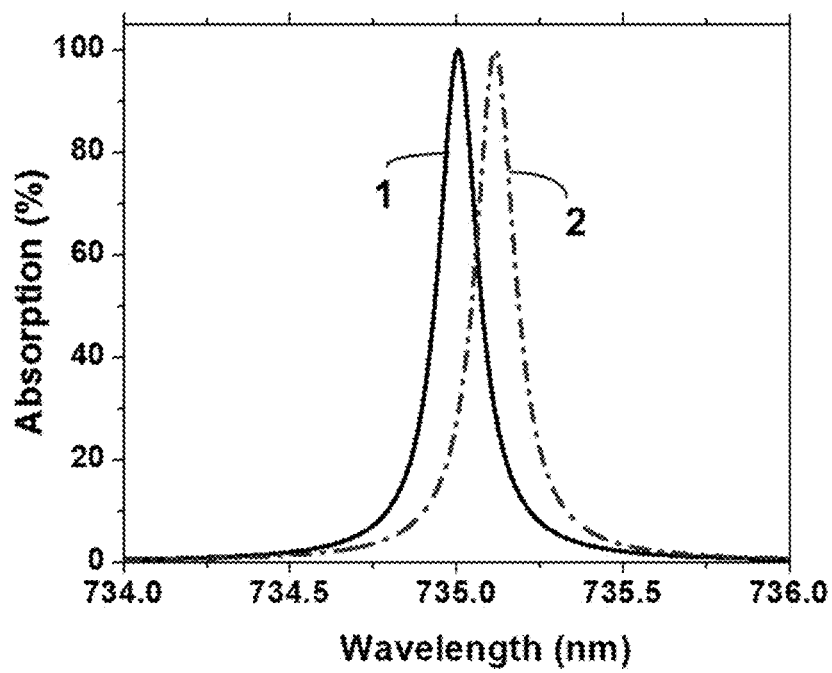
Figure 20B:
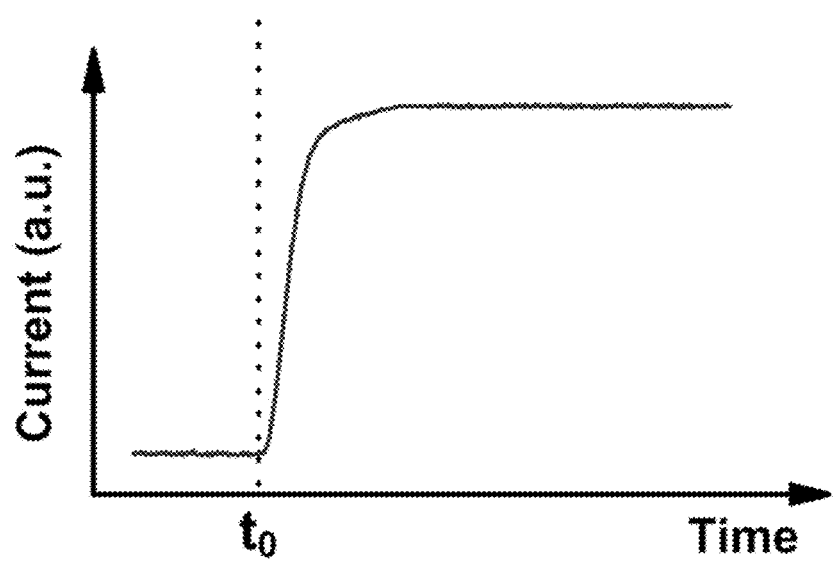

FIG. 20A is the simulated absorption spectra of the IPC structure of FIG. 1 for optical biosensor; FIG. 20B is the schematic of the time-response of the output photocurrent due to analyte adsorbed on the sensor surface.

Figure 21A:
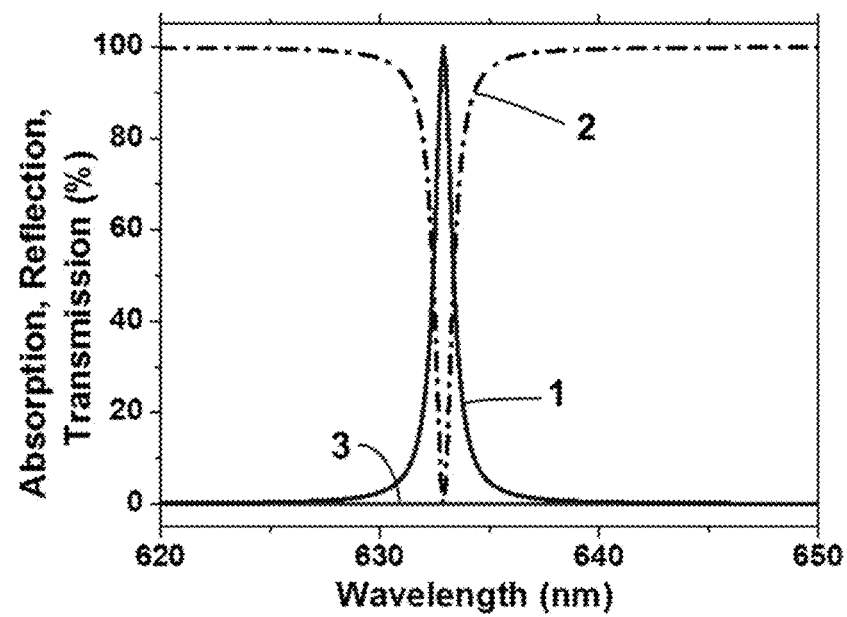
Figure 21B:
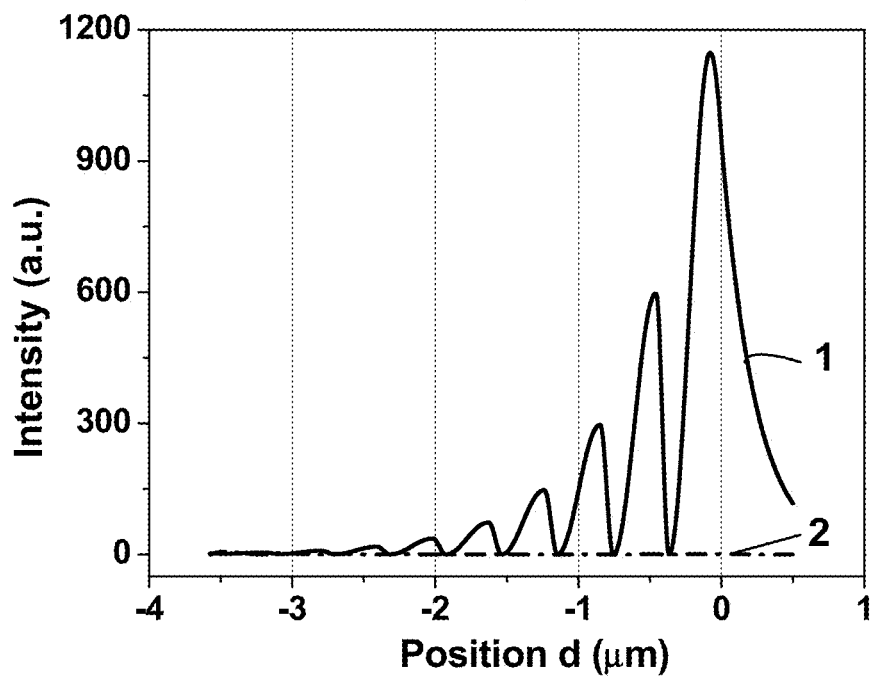

FIG. 21A is the simulated spectra of the IPC structure of FIG. 1 for graphene photodetector; FIG. 21B is the simulated intensity distribution within the IPC-based graphene photodetector.

Corresponding reference numerals indicate corresponding parts throughout the several views of the drawings.

DETAILED DESCRIPTION

Example embodiments will now be described fully with reference to the accompanying drawings.

Referring initially to FIG. 1, an integrated photonic crystal (IPC) structure 10 is schematically illustrated. Generally, the IPC structure 10 includes a photonic crystal structure 14, and a defect member 16 comprising a photoconductive material 18. The defect member 16 is disposed on top of the PC structure 14. Also, a light coupler 12 and a ambient medium 20 (e.g., water, air, or other suitable substance) can be on opposite sides of the PC structure 14 and the defect member 16.

The PC structure 14 can include various shapes, layers or materials. In some embodiment, it can be one-dimensional photonic crystal structure, consisting of alternating pairs of multilayers 42 and 44 with different refractive indices, such as $Si/SiO_2$, $Si_3N_4/SiO_2$, $TiO_2/SiO_2$, GaAs/AlAs, or $Ge/As_2S_3$. The defect member 16 can be of any suitable type and material, such as $SiO_2$, or polymer. The photoconductive material 18 is incorporated in the defect member 16. It can be any suitable structure and material, such as Si, Ge, InGaAs, PbS, PbSe, GaAs, or graphene.

An input light signal 21 is input to the PC structure 14 via the light coupler 12. The light signal 21 can be any suitable electromagnetic wave such as visible light, ultraviolet light, infrared light, gamma radiation, or Terahertz radiation. The light signal 21 can come from a light source (such as laser) or an object. The light signal 21 can be linearly polarized light, preferably s-polarized (TE mode: transverse electric) or p-polarized light (TM mode: transverse magnetic). And it can be preferably be a collimated beam.

An output signal 23 corresponding to the change of a property of the photoconductive material 18 is obtained as a measurable signal. The property of the photoconductive material can be electrical conductivity. The output signal 23 can be any suitable type such as current, resistance, or voltage.

In some embodiments, the IPC structure can be operated as a laser, where the photoconductive material 18 can be any suitable active gain medium (such as GaAs, InGaAs, or GaN), the input light signal 21 can be a pump light, and the output signal 23 can be an excited laser signal.

In some embodiments, the IPC structure 10 can have a total internal reflection (TIR) geometry. Specifically, as illustrated in FIGS. 2A-2C, the light coupler 12, such as a grating, a reflector, or a prism, makes the input light signal propagate at a suitable incident angle into the PC structure 14 and be totally internally reflected between the defect member 16 and the ambient medium 20, where a TIR boundary can be defined at their interface. A Fabry-Pérot (FP) resonant microcavity can form in the defect member 16 due to the high reflectivities provided by both the PC structure 14 and the TIR boundary. The input light signal 21 can be reflected back and forth many times in the FP resonator and get absorbed by the photoconductive material 18 in the microcavity (i.e., the defect member 16). Therefore, an absorption resonance peak forms, representing the FP resonance mode in the microcavity. When some of the properties of the IPC structure 10 (including the defect member 16, the ambient medium 20, the photonic crystal structure 14, or the input light signal 21), the absorption resonance peak shifts and then the absorbed light at a specific wavelength is changed, which is followed by the change of the electrical conductivity of the photoconductive material 18 and correspondingly the change of the output signal 23. Thus the output signal 23 can be used to monitor the change of the properties of the IPC structure 10 correspondingly.

The IPC structure 10, comprising the light coupler 12, the photonic crystal structure 14, the defect member 16, and the photoconductive material 18, can have any suitable configuration in a variety of ways, some of which will be discussed in greater detail below. The following discussion relates to only some of the configurations of the IPC structure 10. It will be appreciated that the IPC structure 10 can also be implemented in other ways without departing from the scope of the present disclosure.

Referring initially to FIG. 2, the purpose of the light coupler is to make an input light signal propagate at a suitable incident angle such that the input light can be internally reflected between the defect member and the ambient medium. In some embodiments, as FIG. 2A shows, a grating 212 can be utilized to diffract an input light signal 221, such that the output light signal 231 is refracted at a desirable angle θ in the photonic crystal structure 214 disposed on top of the grating 212.

The grating coupler can be used for the integrated photonic crystal structure, which allows the IPC structure to work at normal incidence and makes it be a vertically-stacked multilayer structure. The diffracted angle and the coupling efficiency of a grating coupler are dependent on several parameters such as the grating depth, the index modulation of the grating, and the type of grating. In some embodiments, the grating can be a holographic grating or hologram, which can be fabricated in a suitable material, such as photopolymer or photosensitive glass.

In some embodiments, as FIG. 2B shows, a reflector 224' positioned at a suitable oblique angle β within a waveguide 212' can be utilized to reflect an input light signal 221', such that the output light signal 231' is refracted at a desirable angle θ in the photonic crystal structure 214' disposed on top of the waveguide 212'.

In some embodiments, as FIG. 2C shows, a prism can be utilized in the form of Kretschmann-like geometry. An input light signal 221" enters into the prism 212" at an incident angle, such that the output light signal 231" is refracted at a desirable angle θ in the photonic crystal structure 214" disposed on the top of the prism 212". The prism 212" can be of any suitable type or material such as BK 7 glass.

Figure 3A:
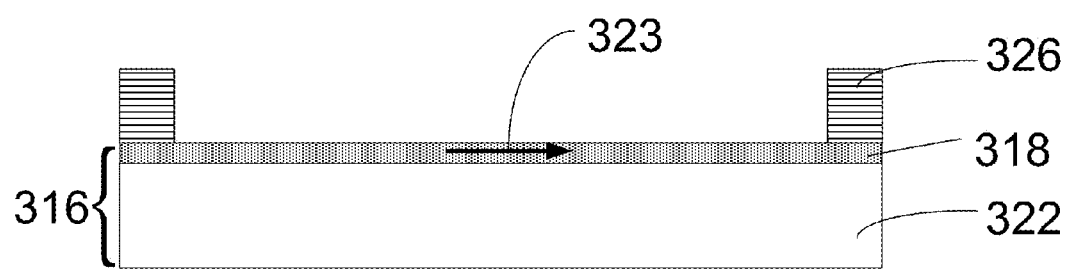
FIGS. 3A-3B are schematic views of a photoconductive material configuration of the IPC structure of FIG. 1 according to additional embodiments of the present disclosure, including: single photoconductive layer (FIG. 3A), and p-i-n layers (FIG. 3B).

Referring initially to FIG. 3, the photoconductive material is a key feature in the IPC structure 10. Its purpose is to absorb an input light signal and to output a signal, monitoring the change of the properties of the IPC structure 10. In some embodiments, as FIG. 3A shows, a single photoconductive layer 318 is incorporated in a defect member 316, with or without an additional part 322 of the defect member 316. Two electrodes 326 can be disposed on two ends of the photoconductive material 318 such that the change of the electrical conductivity of the photoconductive material 318 causes the change of the output signal 323. The photoconductive layer 318 can be any suitable material, such as Si, Ge, InGaAs, PbS, PbSe, or graphene. It can be any suitable structure, such as amorphous, polycrystalline, crystalline, monolayer, p-n, or p-i-n. It can be also any suitable combination of material and structure, such as amorphous Si, polycrystalline PbSe, single graphene layer. It can be at any suitable position of the defect member 316, such as bottom, top, or middle.

Figure 3B:
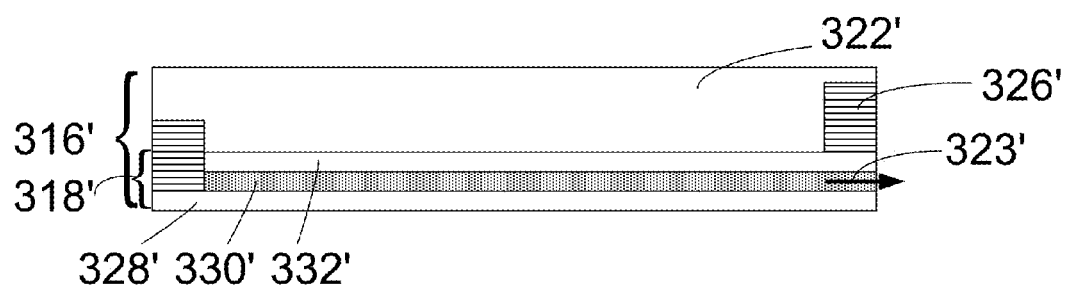

In some embodiments, as FIG. 3B shows, a photoconductive material 318' is a p-i-n photodiode structure, which is composed of a p⁺ implant layer 328', an intrinsic layer 330', and an n⁺ implant layer 332'. Two electrodes 326' are separately disposed on the p⁺ implant layer 328' and the n⁺ implant layer 332', such that the change of the electrical conductivity of the photoconductive material 318' (i.e., p-i-n photodiode structure) causes the change of the output signal 323'. A defect member 316' can comprise the photoconductive material 318' without or with an addition part 322'.

Figure 4A:
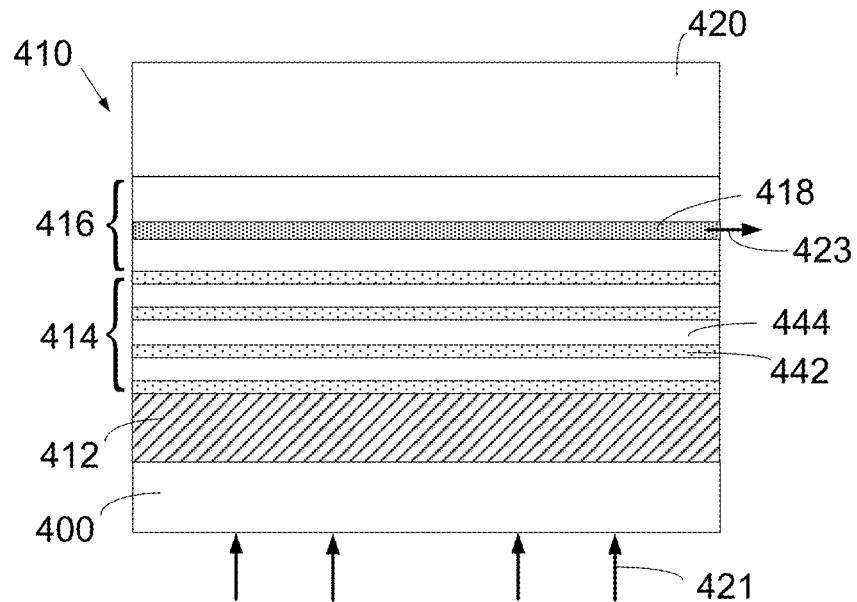
FIGS. 4A-4B are schematic views of the IPC structure of FIG. 1 using grating coupler for integrated configurations according to additional embodiments of the present disclosure, with separate input light signal (FIG. 4A), and with integrated input light signal from a light source (FIG. 4B).

Referring initially to FIG. 4, the IPC structure with a grating coupler for integration is presented. In some embodiments, as shown in FIG. 4A, all the components of the IPC structure 410, including the grating coupler 412, the photonic crystal structure 414 consisting of alternating pairs of multilayers 442 and 444, the defect member 416, the photoconductive material 418, can be vertically disposed on a substrate 400. Therefore, the IPC structure 10 can work at normal incidence, receiving a normal input light signal 421 and outputting an output electrical signal 423.

Figure 4B:
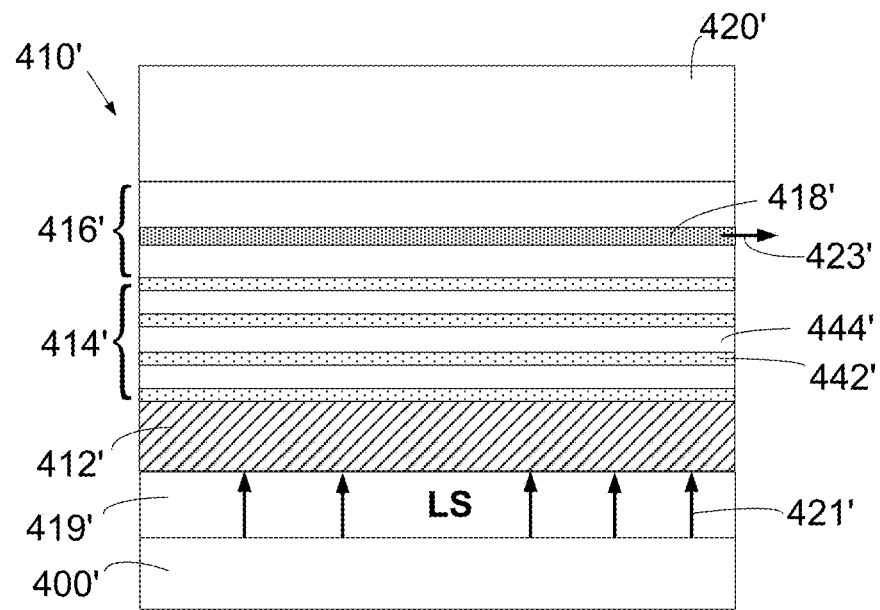

In some embodiments, a light source can be also integrated into the IPC structure. As shown in FIG. 4B, a light source 419' emitting a normal incident light signal 421', is disposed between a grating coupler 412' and a substrate 400'. Therefore, a fully-integrated photonic crystal structure 410', including the light source 419', the grating coupler 412', the photonic crystal structure 414' consisting of alternating pairs of multilayers 442' and 444', the defect member 416', the photoconductive material 418', can be vertically disposed on a substrate 400', outputting an output electrical signal 423', which is highly desirable for diverse applications.

Figure 5A:
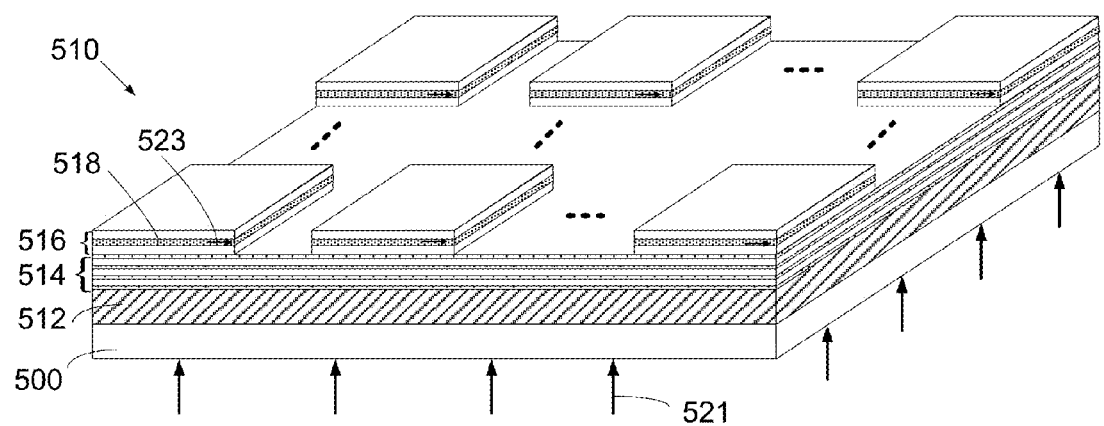
FIGS. 5A-5B are schematic views of array configurations using the IPC structure of FIG. 1 and the grating coupler of FIG. 2B according to additional embodiments of the present disclosure, with shared PC structure (FIG. 5A), and with individual PC structure (FIG. 5B).

Referring initially to FIG. 5, an array using an IPC structure as illustrated in FIG. 1 and a grating coupler as illustrated in FIG. 2A is presented. In some embodiments, as shown in FIG. 5A, each transducer element shares a same substrate 500, a same grating coupler 512, and a same photonic crystal structure 514, but has individual defect member 516 incorporating a photoconductive material 518, such that each transducer element works independently and has individual output signal 523. An input light signal 521 is propagating into the array 510 at normal incidence. The array 510 can have any suitable configuration in one-dimension (1D), two-dimensions (2D), or three-dimensions (3D).

Figure 5B:
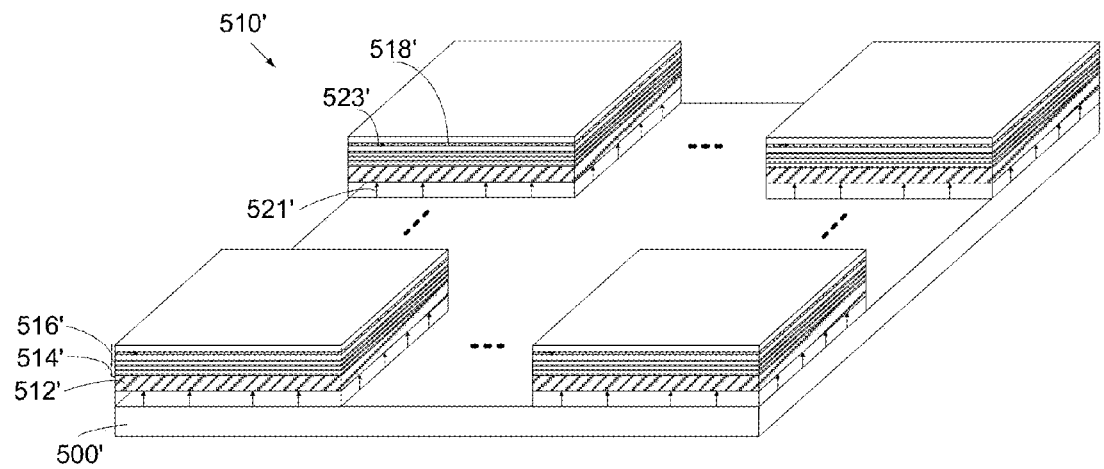

In some embodiments, as shown in FIG. 5B, each transducer element can also have individual input light signal 521', individual grating coupler 512', individual photonic crystal structure 514', individual defect member 516' with a photoconductive material 518', and individual output signal 523'. All the transducer elements are disposed on a same substrate 500' with a suitable array configuration in 1D, 2D, or 3D.

Figure 6A:
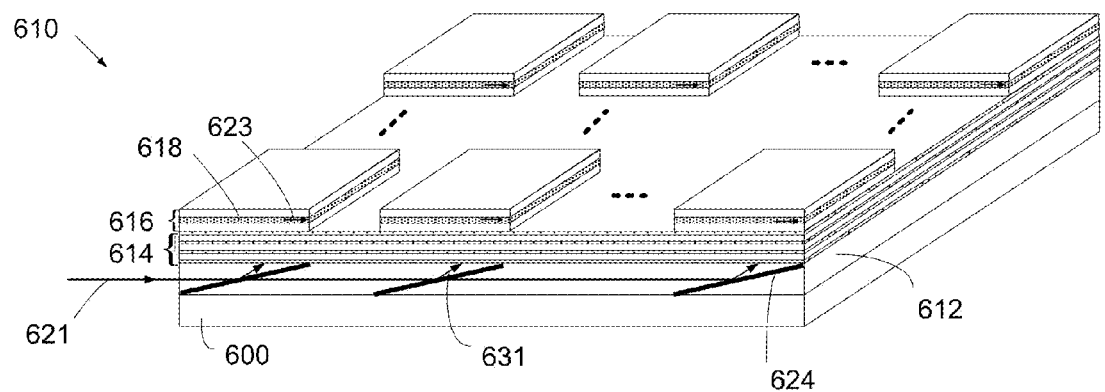
FIGS. 6A-6B are schematic views of array configurations using the IPC structure of FIG. 1 and the reflector coupler of FIG. 2C according to additional embodiments of the present disclosure, with shared PC structure (FIG. 6A), and with individual PC structure (FIG. 6B).

Referring initially to FIG. 6, an IPC structure array can also use a reflector coupler in a waveguide as illustrated in FIG. 2B. In some embodiments, as shown in FIG. 6A, each transducer element in an IPC structure array 610 can have individual reflector 624 providing a suitable reflected light 631, individual defect member 616 incorporating a photoconductive material 618, but share a same photonic crystal structure 614, a same waveguide 612, and a same substrate 600. An input light signal 621 is entering the waveguide 612 and reflected by individual reflector 624 to individual transducer element, which has an individual output signal 623.

Figure 6B:
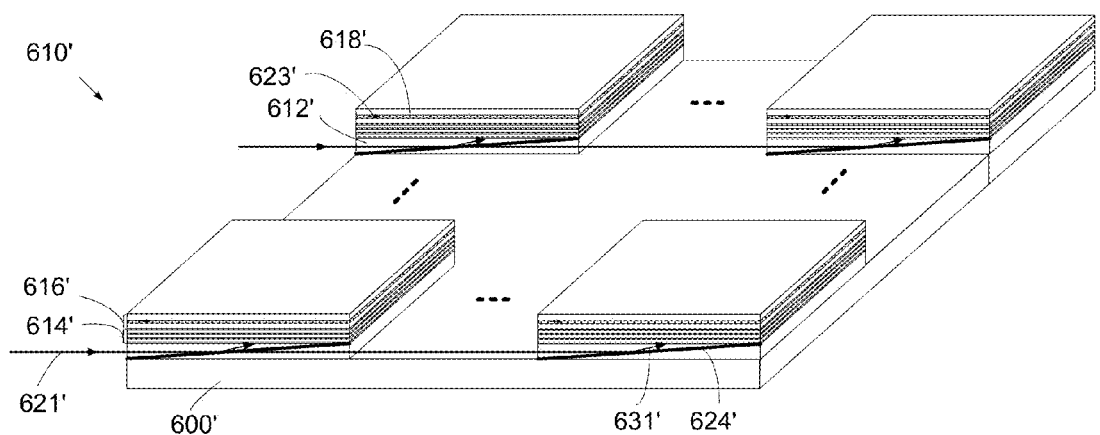

In some embodiments, as shown in FIG. 6B, each transducer element in an IPC structure array 610' can also have individual reflector 624', photonic crystal structure 614', and defect member 616' incorporating a photoconductive material 618'. They may have individual waveguide 612' or shared waveguide, which are deposited on a same substrate 600'. A horizontal input light signal 621' is entering the waveguide 612' and reflected by individual reflector 624' to individual transducer element, which has an individual output signal 623'.

Figure 7A:
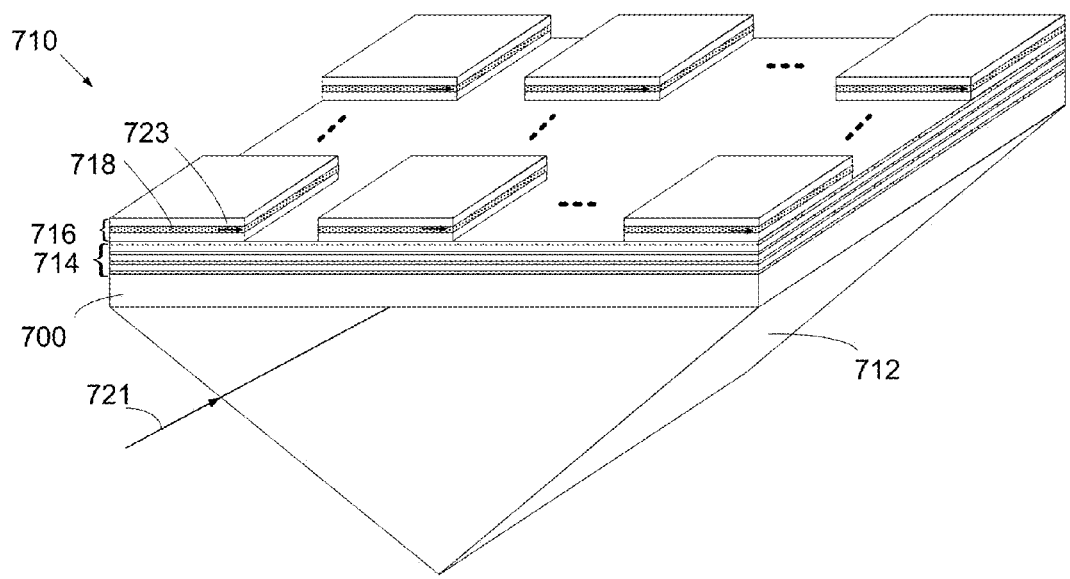
FIGS. 7A-7B are schematic views of array configurations using the IPC structure of FIG. 1 and the prism coupler of FIG. 2A according to additional embodiments of the present disclosure, with shared PC structure (FIG. 7A), and with individual PC structure (FIG. 7B).

Referring initially to FIG. 7, an IPC structure array 710 can also be realized using a prism coupler as illustrated in FIG. 2C. In some embodiments, as shown in FIG. 7A, each transducer element has individual defect member 716 incorporating a photoconductive material 718 that obtains an individual output signal 723, but share a same photonic crystal structure 714. All the transducer elements are disposed on a substrate 700, which is disposed on the top of a prism coupler 712. In some embodiments, an index matching medium may be used between the prism 712 and the substrate 700. In some embodiments, the IPC structure can be directly disposed on the prism without the substrate 700. An input light signal 721 is incident at an oblique angle into the prism 712. It is to be noted that the light probe beam size should be large enough to cover all the working transducer elements.

Figure 7B:
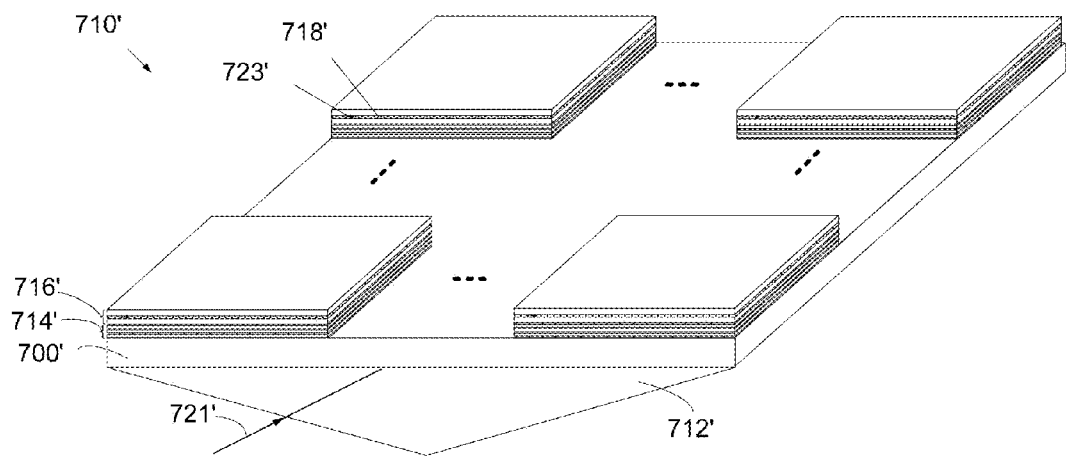

In some embodiments, as shown in FIG. 7B, each transducer element works similar to that shown in FIG. 7A indicated with corresponding reference numerals by adding an apostrophe symbol ', except that they have individual photonic crystal structure 714'.

Mechanism of Using IPC Structure

Operation of the integrated photonic crystal (IPC) structure 10 as illustrated in FIG. 1 is now explained in greater detail. The IPC structure 10 integrates a light coupler 12 to diffract an input light signal 21 at a specific angle so that TIR occurs between the defect member 16 and the ambient medium 20, where a TIR boundary can be defined at their interface. In some embodiments, the photonic crystal structure 14 can consist of alternating pairs of higher-index layer 42 and lower-index layer 44. In order to form a photonic bandgap, the thicknesses of the lower-index layers 44 and higher-index layers 42 should satisfy $$n_A d_A \cos\theta_A = n_B d_B \cos\theta_B = \lambda_R/4$$

where $n_A$, $n_B$ represent the effective refractive indices of the lower and higher index layers, respectively; $d_A$, $d_B$ represent the physical thicknesses of the lower and higher index layers, respectively; $\theta_A$, $\theta_B$ are the refractive angles in the lower and higher index layers, respectively; $\lambda_R$ is the resonant wavelength.

Since the TIR boundary and the photonic crystal structure 14 both can provide high reflectivities, a Fabry-Pérot (FP) resonator can form in the defect member 16, if the properties of the defect member 16 satisfy the following resonant condition:

$$2\frac{2\pi}{\lambda_R}n_x d_x \cos\theta_x + \alpha = (2m+1)\pi$$

$$(m = 0, 1, 2, \ldots)$$

where $n_x$ and $d_x$ represent the effective refractive index and physical thickness of the defect member 16, respectively. $\theta_x$ is the refractive angle in the defect member 16, $\lambda_R$ is the resonant wavelength, and $\alpha$ represents the Goos-Hänchen phase shift between the defect member 16 and the ambient medium 20.

In the IPC structure 10, a photoconductive material 18 is intentionally incorporated in the defect member 16 (i.e. the FP microcavity). Only light resonant with the FP resonator can be absorbed in the photoconductive material 18, and off-resonant light is totally reflected back by the photonic crystal structure 14. Thus, the absorption spectrum will show a pronounced peak at the resonance wavelength. When some of the properties of the IPC structure 10 (including the defect member 16, the ambient medium 20, the photonic crystal structure 14, or the input light signal 21), the resonance wavelength of the FP resonator will shift, so does the absorption resonance peak. At a specific wavelength, the absorbed intensity in the photoconductive material can also change, which is followed by the change of the electrical conductivity of the photoconductive material 18 and corresponding change of the output signal 23. Therefore, the output signal 23 can be used to monitor the change of the properties of the IPC structure 10 correspondingly. Since a lot of external influences (including those to be discussed below) can change the properties of the IPC structure 10, such as an ambient medium change, a light signal change, a pressure input, an acoustic input, an ultrasonic input, and materials adsorbed on the surface, the IPC structure 10 can be explored for diverse applications.

Moreover, the unique configuration of the IPC structure provides many distinctive advantages: (1) The integration of the photoconductive material can directly turn light signal into electrical signal for output, eliminating the requirement for additional photodetectors; (2) The defect member is open to the ambient environment, defining an operative surface for diverse applications; (3) The high finesse Fabry-Pérot resonator formed in the defect member ensures high performance for signal transduction; (4) The photonic crystal structure, together with suitable photoconductive materials, can be designed to work at any suitable wavelength; (5) The photonic crystal structure combines both the sensing transducer and the detection element (i.e., photodetector), constructing compact and integrated systems; (6) The integrated photonic crystal structure can be a vertically-stacked multilayer structure, which can be easily fabricated into high density array devices with standard technologies (e.g., fabrication technologies for thin film coating, silicon, or complementary metal-oxide-semiconductor (CMOS)).

The IPC structure 10 can be used in a variety of ways, some of which will be discussed in greater detail below. The following discussion relates to only some of the applications and uses of the IPC structure 10. It will be appreciated that the IPC structure 10 can also be implemented in other ways without departing from the scope of the present disclosure.

Exemplary Devices of IPC Structure

Figure 8:
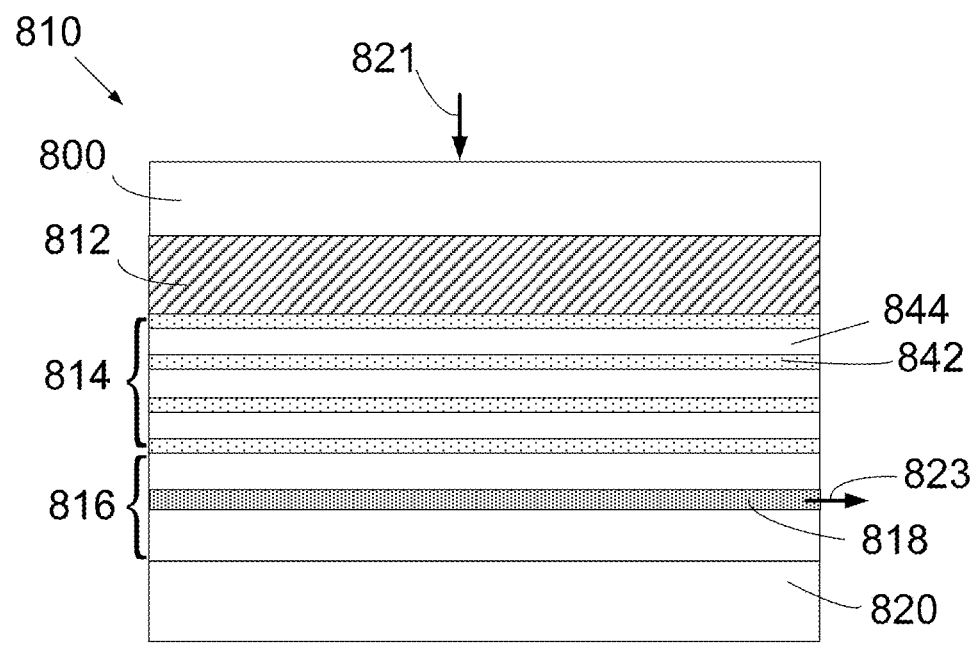
FIG. 8 is schematic views of the IPC structure of FIG. 1 for a photodetector with a grating coupler as illustrated in FIG. 2A according to additional embodiments of the present disclosure.

Referring to FIG. 8, the IPC structure 10 implemented in a photodetector is illustrated according to various additional embodiments. In some embodiments, as shown in FIG. 8, an input light signal under test 821 is incident onto an IPC structure 810, whose components are similar to the embodiments illustrated in FIG. 4A, indicated with corresponding reference numerals increased by 400. The ambient medium 820 is preferable to be air. The IPC structure 810 can be used to detect a change of an input light signal, including the intensity change, the wavelength change, and the polarization change, if the wavelength of the input light signal is within the resonance peak. Similarly, a reflector or prism coupler can be also utilized in the IPC structure to implement a photodetector.

Referring to FIG. 9, the IPC structure 10 implemented in an acoustic or ultrasonic sensor is illustrated according to various additional embodiments. The sensing principle is briefly explained here. When an incoming acoustic (or sound) or ultrasonic (abbreviated as S/W) wave is incident on the defect member 16, the acoustic or ultrasonic pressure can change the properties of the defect member 16 (such as refractive index or thickness), thus the resonant condition in the defect member 16 changes and the resonant wavelength shifts, which can be detected by monitoring the output signal 23.

Figure 9A:
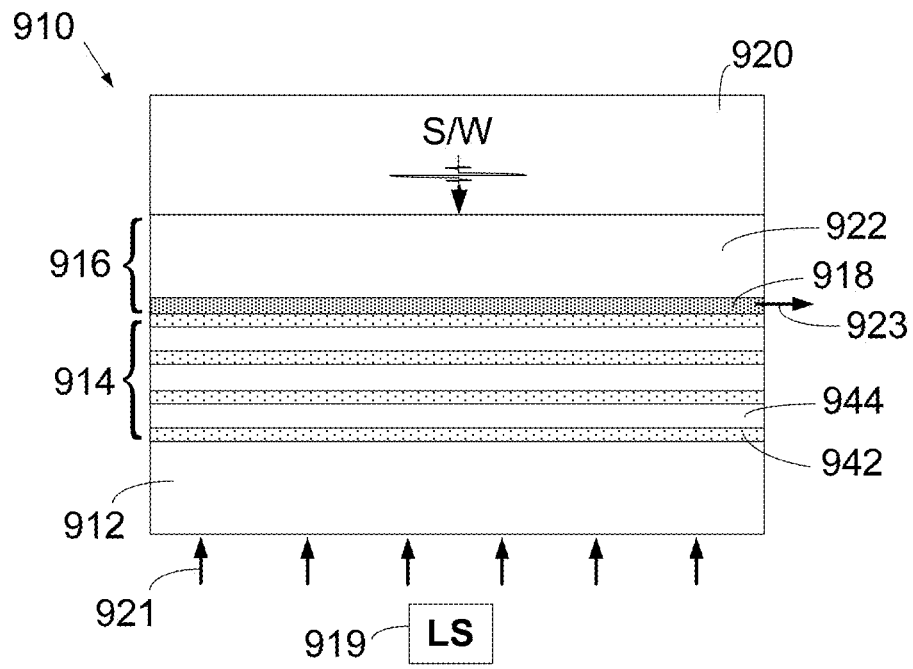
FIGS. 9A-9B are schematic views of the IPC structure of FIG. 1 for an acoustic/ultrasonic receiver with configurations of FIG. 4A-4B according to additional embodiments of the present disclosure, with separate light source (FIG. 9A), and with integrated light source (FIG. 9B).

In some embodiments, as shown in FIG. 9A, the IPC structure 910 has components that are similar to the embodiments illustrated in FIG. 1 indicated with corresponding reference numerals increased by 900. The defect member 916 is composed of a photoconductive layer 918 and a sensing layer 922. The sensing layer 922 can be made of any suitable material, such as polydimethylsiloxane (PDMS) or polymethyl-methacrylate (PMMA). The photoconductive layer 918 can be at any position within the defect member 916, preferably at the bottom adjacent the photonic crystal 914. The acoustic or ultrasonic wave under test is incident directly onto the sensing layer 922 in the defect member 916.

Figure 9B:
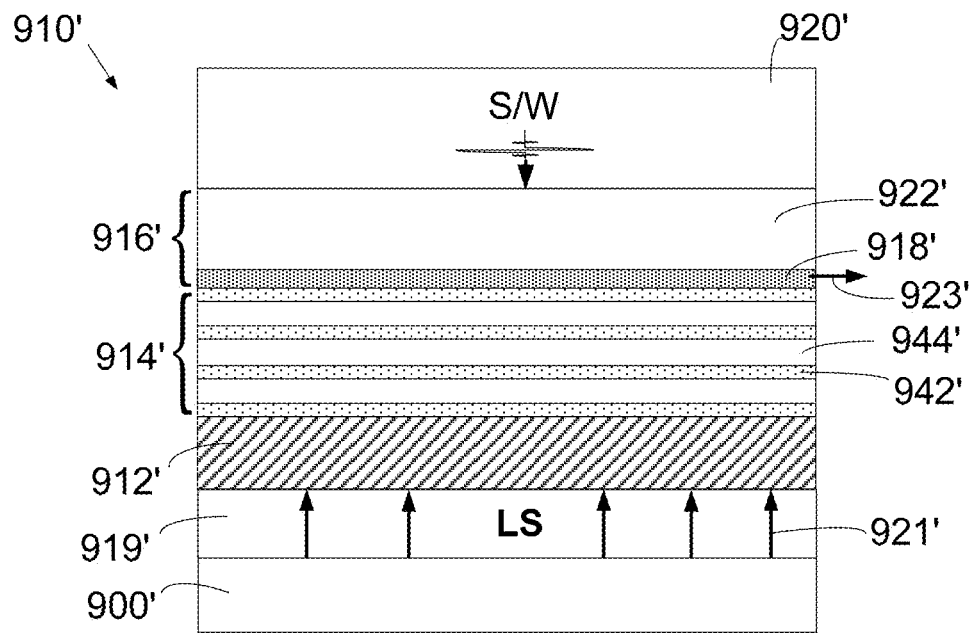

In some embodiments, as shown in FIG. 9B, the IPC structure 910' can integrate a light source 919' for acoustic or ultrasonic sensor. It has components that are similar to the embodiments of FIG. 4B indicated with corresponding reference numerals increased by 500. In addition, the defect member 916' has a preferable configuration same as the defect member 916.

Figure 10:
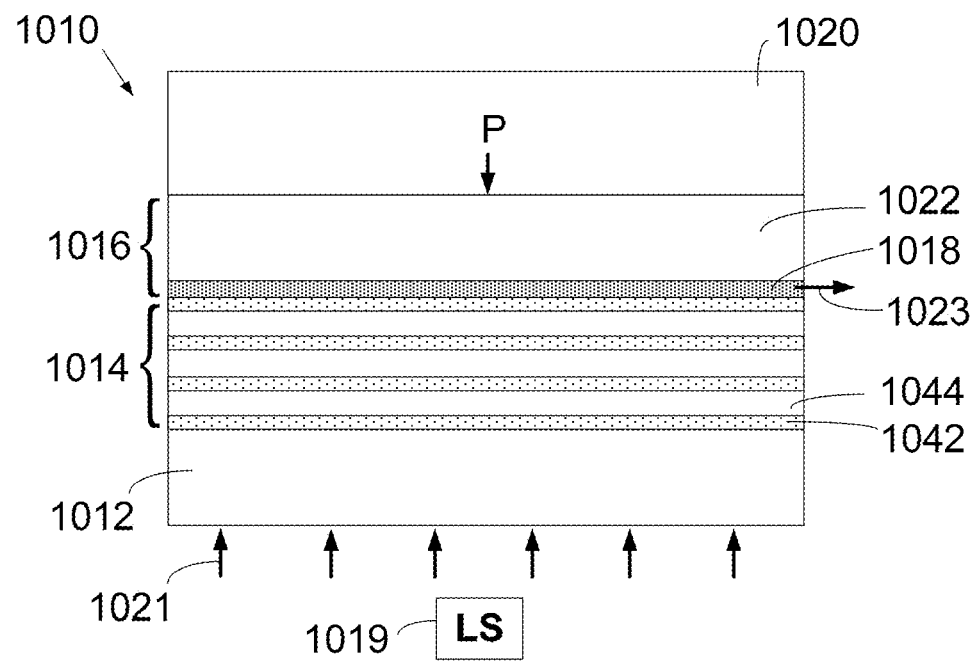
FIG. 10 is a schematic view of the IPC structure of FIG. 1 for a pressure sensor according to additional embodiments of the present disclosure.

Referring to FIG. 10, the IPC structure 10 implemented in a pressure sensor is illustrated according to various additional embodiments. The sensing principle is briefly explained here. When an incoming pressure is incident on the defect member 16, the pressure will change the properties of the defect member 16 (such as refractive index or thickness), thus the resonant condition in the defect member 16 changes and the resonant wavelength shifts, which can be detected by monitoring the output signal 23.

In some embodiments, as shown in FIG. 10, the IPC structure 1010 can have components that are similar to the embodiments illustrated in FIG. 9A indicated with corresponding reference numerals increased by 100. Moreover, it can also be integrated with a light source, similar to the embodiment of FIG. 9B.

Figure 11:
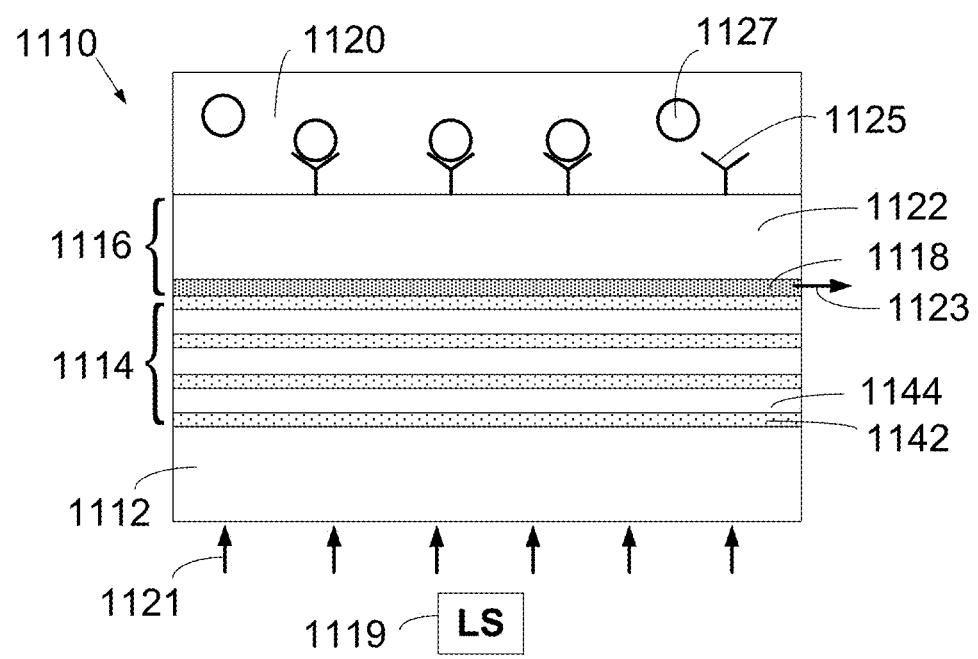
FIG. 11 is a schematic view of the IPC structure of FIG. 1 for a biosensor according to additional embodiments of the present disclosure.

Referring to FIG. 11, the IPC structure 10 implemented in a biosensor is illustrated according to various additional embodiments. The sensing principle is briefly explained here. When some material is adsorbed onto or desorbed from the surface of the defect member 16, or the biological characteristics of the ambient medium 20 changes, the resonant condition in the defect member 16 changes and the resonant wavelength shifts, which can be detected by monitoring the output signal 23.

In some embodiments, as shown in FIG. 11, the IPC structure 1110 can have components that are similar to the embodiments of FIG. 1 indicated with corresponding reference numerals increased by 1100. A photoconductive layer 1118 can be at any position within a defect member 1116. When the photoconductive layer 1118 is at the bottom, the additional part 1122 of the defect member 1116 provides an operative surface for biosensors. The surface can be functionalized to immobilize ligand molecules 1125, which can capture analyte molecules 1127 adsorb onto the surface. The additional part 1122 of the defect member 1116 can be any suitable material (such as $SiO_2$) and any shape (continuous layer or porous structure). When the photoconductive layer 1118 on the top of the defect member 1116, the photoconductive layer provides an operative surface, which can be also functionalized for biosensors.

In the following, the applications of the integrated photonic crystal (IPC) structures and devices described in the figures above will be discussed in connection with a number of exemplary systems in greater detail.

Exemplary System 1

Flexible Acoustic Transducer Array

Figure 12:
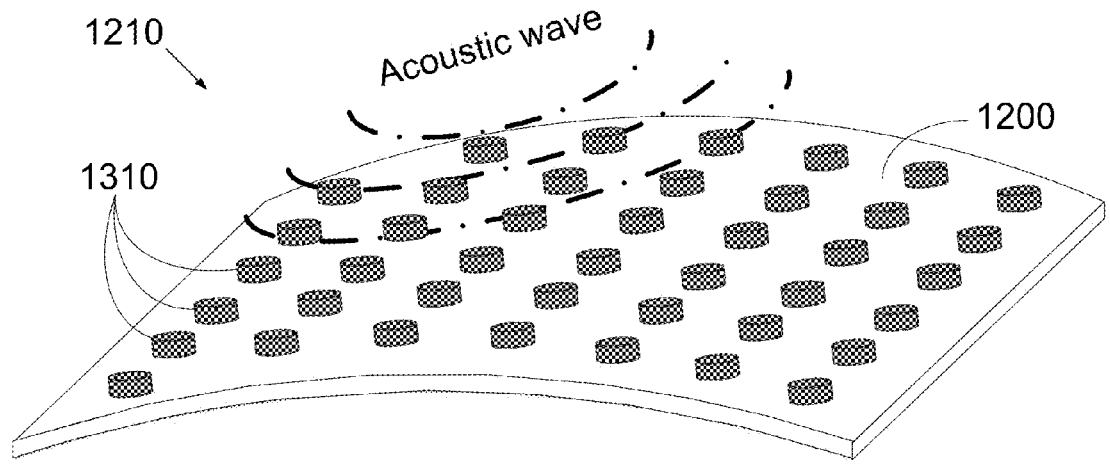
FIG. 12 is a schematic view of the IPC structure of FIG. 1 for a flexible acoustic transducer array according to additional embodiments of the present disclosure.
Figure 13:
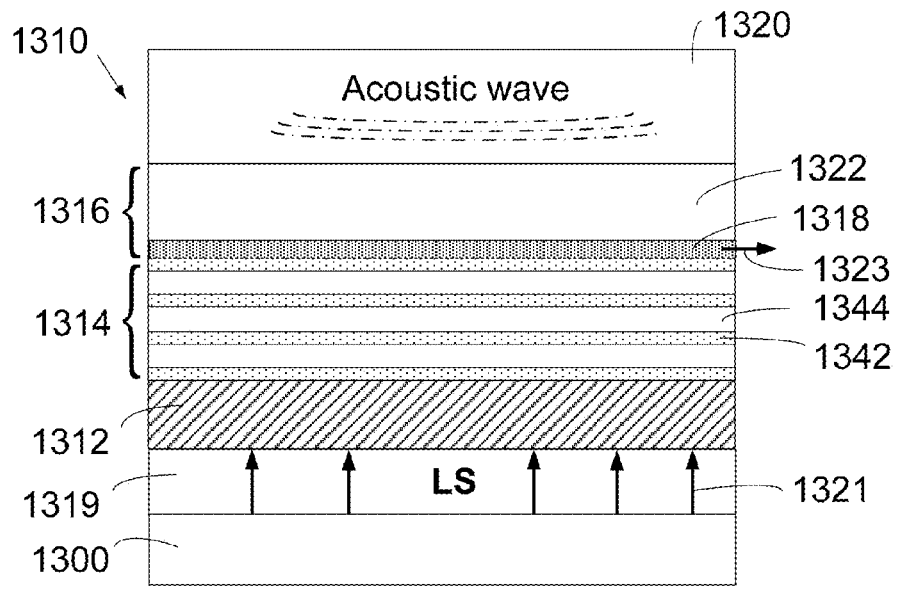
FIG. 13 is a schematic view of the IPC structure of FIG. 1 for an optical acoustic transducer according to additional embodiments of the present disclosure.

This example is to apply the integrated photonic crystal structure 10 as illustrated in FIG. 1 for flexible acoustic transducer arrays. FIG. 12A schematically shows a flexible acoustic transducer array 1210, which comprises an array of optical acoustic transducer 1310 made of the IPC structure on a flexible substrate 1200. The optical acoustic transducer 1310 as illustrated in FIG. 13 has a similar embodiment to 910' illustrated in FIG. 9B.

As a key element of acoustic reconnaissance, acoustic transducer arrays provide directionality, high signal gain, and effective noise reduction, which have potential to greatly enhance the capabilities of target detection and tracking, localization and classification of noise sources, mission-specific and combat vehicles deployed in high-threat environments. However, the unavailability of miniaturized acoustic transducers significantly restricts their applications in the battlefield, as the transducer size directly determines the detection spatial resolution and bandwidth. Moreover, compact acoustic transducers could be mounted on curved surfaces, which is very attractive and will greatly broaden their applications. Therefore, it is highly desirable to develop a transducer that can form compact acoustic transducer arrays on flexible substrates. Such an ideal acoustic transducer should be small, thin, flexible, passive; have low noise floor; be highly sensitive to acoustic pressure with linear and flat response within audio frequency (20 Hz to 20 kHz); as well as being low cost, light-weight, easy to fabricate into an array, and with minimal power consumption.

Among all the existing transduction methods including capacitive, piezoresistive, and piezoelectric, piezoelectric transduction is the most promising one to meet the stringent needs. Recent developments, including microelectromechanical systems (MEMS) piezoelectric microphones and nanostructured piezoelectric acoustic sensors, have drastically reduced the transducer size down to 250 μm in diameter. However, due to the inherent thermal noise in piezoelectric systems, the reduction of transducer size results in increased noise floor, thus leading to a poor sensor performance. Moreover, MEMS piezoelectric transducers are electrical/mechanical based devices, consisting of many complicated capacitive and resistive components, which make them suffer from narrow flatband response and insensitivity to low acoustic frequency (<50 Hz). As competitive techniques, optics-based methods have also been explored for acoustic detections. One of their advantages over piezoelectric transduction is that their sensitivity is independent of the size of the diaphragm membrane. However, a significant challenge in the development of miniaturized optical acoustic sensors has been the integration of the mechanical structures with light sources and light detectors in a small volume. To date, the smallest packaged single optical MEMS microphone with diffraction-based optical displacement detection is contained in more than 1 $mm^3$ volume with a noise floor of 28 dB sound pressure level (SPL). Obviously, no existing acoustic transducer can simultaneously satisfy all the requirements of the ideal acoustic transducer.

However, the optical acoustic transducer 1310 of the present disclosure fundamentally overcomes the limitation of the trade-off between transducer size and minimum detectable pressure (MDP) that all existing acoustic transducers encounter. It can achieve smaller size and lower MDP simultaneously. Moreover, it makes use of polymer with low Young's modulus as the sensitive layer 1322 (i.e., the additional part of defect member 1316) for ultra-sensitive acoustic response. Consequently, optical detection for broad-band frequency operation (20 Hz to 20 kHz) can be realized with integrated light sources 1319 and integrated photodetectors (made of the photoconductive layer 1318) for miniaturized systems with low power consumption. The optical acoustic transducer 1310 is a vertically-stacked multilayer structure, and can be easily fabricated into two dimensional arrays with low cost and high throughput while maintaining performance superiority. The optical acoustic transducer 1310 of the present disclosure can be developed as a miniaturized optoacoustic transducer on a flexible substrate (such as Kapton, or PET), achieving low MDP (<10 dB SPL), small size (<50 μm), high sensitivity (>1 mV/Pa), and a broad frequency operation range (20 Hz to 20 kHz).

The operating principle is now described with greater details. When an incoming acoustic wave arrives the optoacoustic transducer 1310, the acoustic pressure $\Delta P$ will change the thickness of the sensitive layer 1322, so as the effective thickness $d_x$ of the defect layer 1316, and the strain $\in_x$ is estimated to be:

$$\in_x = \Delta d_x / d_x = -\Delta P / E$$

where E is the Young's modulus of the sensing material.

Figure 14A:
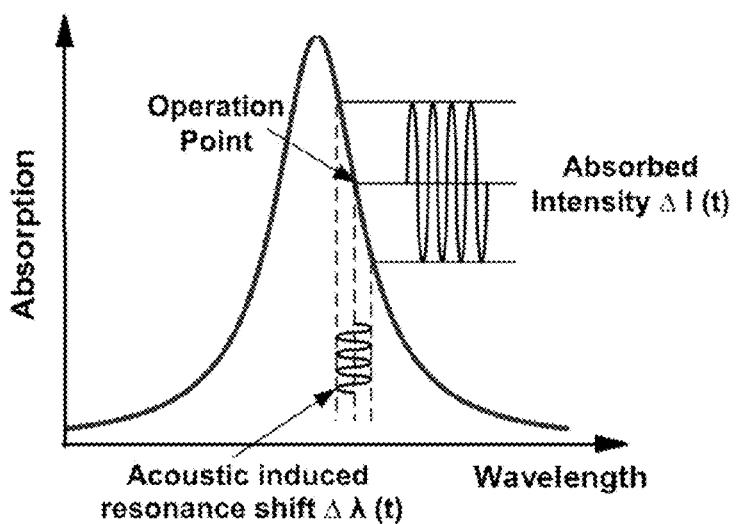
FIG. 14A is a schematic of the operating principle of the IPC structure of FIG. 1 for an optical acoustic transducer.

When the effective thickness of the defect layer 1316 changes, the resonance wavelength of the Fabry-Pérot resonator shifts. At a specific wavelength, the absorbed intensity in the photoconductive layer 1318 will also change, as illustrated in FIG. 14A. Since the photodetector is made of the photoconductive layer 1318, its output photocurrent signal 1323 will change correspondingly. Therefore, the incident acoustic wave can be detected by monitoring the photocurrent change.

In the following, the performance of the optoacoustic transducer 1310, including detection sensitivity, noise floor, frequency response, and effective element size, is discussed in greater detail.

The overall detection sensitivity S of the optoacoustic transducer 1310 depends on four factors: the conversion efficiency of acoustic pressure to the defect layer thickness change (acoustic pressure sensitivity As), the conversion efficiency of defect layer thickness change to the resonant wavelength shift (shift sensitivity Bs), the conversion efficiency of resonant wavelength shift to the absorbed intensity change (optical sensitivity Os), and the conversion efficiency of absorbed intensity change to the output photocurrent change (photodiode responsivity Rs).

The optical sensitivity Os (μW/nm) is defined as the absorbed optical power modulation per unit wavelength shift at the operation point $\lambda_0$ of the transducer. Since the resonant absorption peak can be fit by a Lorentzian curve, the maximum optical sensitivity is given by $$O_s\Big|_{max} = \left[\frac{dI_r}{d\lambda}\right]_{\lambda_0}\Bigg|_{max} = \pm 1.3 \frac{I_0}{\Delta\lambda_{res}}$$

where $I_0$ is the incident laser intensity, and $\Delta\lambda_{res}$ is the resonant width of the absorption peak.

The acoustic pressure sensitivity As (nm/Pa) can be expressed as:

$$A_S = \Delta d_x / \Delta P = -d_x / E$$

In addition, the shift sensitivity Bs (nm/nm) is related to the whole structure, and can be calculated by transfer matrix simulation. The photodiode responsivity Rs (μA/μW) can be obtained by measuring the output current response to the input optical power. Therefore, the maximum overall transducer sensitivity S (μA/Pa) can be derived as:

$$S_{max} = \frac{\partial A}{\partial P} = \frac{\partial A}{\partial I_{abs}} \frac{\partial I_{abs}}{\partial \lambda_{res}} \frac{\partial \lambda_{res}}{\partial d_x} \frac{\partial d_x}{\partial P} = R_s \cdot O_s \cdot B_s \cdot A_s = \mp 1.3 \frac{I_0}{\Delta \lambda_{res}} \cdot \frac{d_x}{E} \cdot B_S \cdot R_S$$

In order to achieve high sensitivity of the optoacoustic transducer 1310, high incident laser intensity, high responsivity, a narrow resonance peak, large polymer thickness and resonance shift sensitivity, and polymer with low Young's modulus, are preferable.

In some embodiments, to obtain high sensitivity around the operative wavelength of 850 nm, the IPC structure of the optical acoustic transducer 1310 is built as follows: substrate/laser/grating/$Si_3N_4$/($SiO_2$/$Si_3N_4$)$^6$/Si/PDMS/Air. The PC structure 1314 is made of 6.5 pairs of alternating 126-nm $Si_3N_4$ layer and 221-nm $SiO_2$ layer; the photoconductive layer 1318 is 186-nm polycrystalline Si film with 83-nm p-Si, 20-nm i-Si, and 83-nm n-Si; and the sensing layer 1322 is 4.1-μm PDMS transparent film with a low Young's modulus (E=4 kPa). The diffracted angle out of the grating coupler 1312 is 45°. Transfer matrix simulation shows that the resonance peak width $\Delta\lambda_{res}$ is 0.25 nm, and the shift sensitivity Bs is 0.08 nm/nm. Assuming that the designed photodiode has a typical responsivity of 0.3 μA/μW and that the incident laser intensity $I_0$ is 1 mW, the optoacoustic transducer 1310 sensitivity $S_{max}$ will be 128 μA/Pa or 6.4 mV/Pa with a typical load resistance of 50Ω, which is 2 to 3 orders of magnitude higher than that of the state-of-the-art MEMS piezoelectric transducers.

The noise floor of an acoustic transducer 1310 dictates the smallest input pressure resolvable at its output (i.e., minimum detectable pressure (MDP)). The MEMS piezoelectric transducers are electrical and mechanical/acoustic systems where thermal noise is the intrinsic noise source and restricts their MDPs. In contrast, the optical acoustic transducer 1310 is optical-based method, and its MDP is mainly determined by the noise from the photodiode (e.g., dark current) and the incident laser intensity fluctuation.

First, the dark current of the photodiode can be obtained by measuring the output current with different bias voltage (i.e., I-V characteristics). Previous resonant cavity enhanced (RCE) Si p-i-n photodiodes typically has dark current values of less than 1 μA/cm² at 1V reverse bias. Thus, within a small detection area (e.g., 50-μm diameter), the Si photodiode in the optical acoustic transducer 1310 can get a dark current of about 20 pA. With a sensitivity of 128 μA/Pa, the MDP is 0.16 μPa or −42 dB SPL at this noise level, much smaller than 0 dB SPL.

Second, the laser intensity fluctuation is the dominant noise source for the optical acoustic transducer 1310. However, it can be greatly suppressed by self-referencing or by using a reference channel. Since the acoustic signal is less than 1 second, a noise floor after suppression can be less than $10^{-6}$. Following the discussion above, the fluctuation $10^{-6}$ of the incident laser intensity (10=1 mW) will give a MDP of 0.2 μPa or −40 dB SPL, also much smaller than 0 dB SPL.

Therefore, the optical acoustic transducer 1310 is not limited by thermal noise or the element size. With a suitable architecture, its MDP is expected to be much better than 10 dB SPL, which is superior to any existing acoustic transducers. In some embodiments, the optical acoustic transducer 1310 can be customized to provide a suitable sensitivity as well as minimizing the ambient noise.

The frequency response is an important characteristic parameter for an acoustic transducer. For piezoelectric transducers or some optical microphones using silicon diaphragms, their systems can be considered to be a combination of complicated capacitive and resistive components, which make them suffer from narrow flatband response and insensitive to low acoustic frequency (<50 Hz). For the optical acoustic transducer 1310, the displacement due to the acoustic pressure is mainly from the thickness change of the sensitive layer 122 (e.g., polymer layer), thus, the frequency response is dependent upon the acoustic properties of the polymer layer, the backing material and the ambient medium, which can be derived as:

$$|P(k)| = \frac{T\sqrt{2}}{Nkd_x} \sqrt{\frac{(1+R_1^2)(1-\cos(kd_x))+4R_1\cos(kd_x)\sin^2(kd_x/2)}{1-2R_1R_2\cos(2kd_x)+(R_1R_2)^2}}$$

where k=2πf/v is the acoustic wave number, f is the acoustic frequency and v is the acoustic wave traveling speed in the polymer layer. N is the normalization factor, T is the pressure-amplitude transmission coefficient; $R_1$ and $R_2$ are the pressure-amplitude reflection coefficients at the two surfaces of the polymer layer.

Figure 14B:
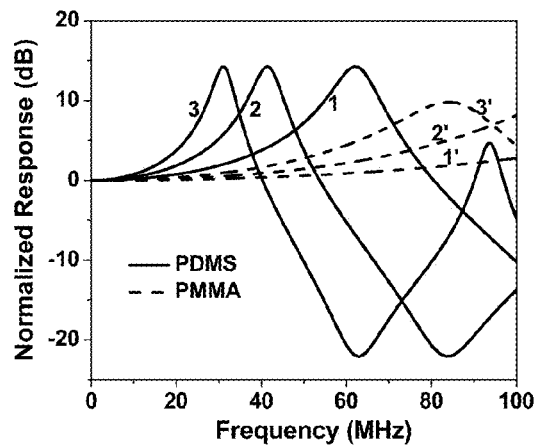
FIGS. 14B-14C is the simulated frequency response of the IPC structure of FIG. 1 for an optical acoustic transducer, including: in MHz range (FIG. 14B), and in kHz range (FIG. 14C).
Figure 14C:
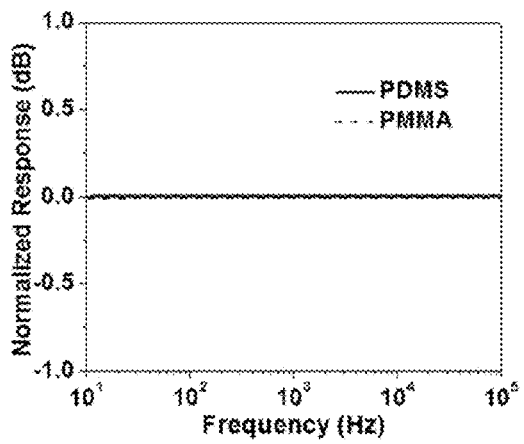

FIG. 14B shows the simulated frequency response with different thickness of PDMS (solid line) and PMMA (dash line) as the sensing layer. From 1 to 3, the PDMS layer thicknesses are 4.00, 6.00, 8.00 μm; from 1' to 3', the PMMA layer thicknesses are 4.00, 6.00, 8.00 μm. It indicates that the resonant frequency increases with thinner thickness and higher Young's modulus ($E_{PMMA}$>$E_{PDMS}$). However, in any of these cases, the optical acoustic transducer 1310 has a resonant frequency far beyond 1 MHz, and has a very flat response within low frequency range, including 20 Hz to 20 kHz, as illustrated in FIG. 14C.

The effective element size is a measure of the acoustic aperture of a transducer. Its effect on lateral spatial resolution makes it a key parameter in acoustic sensing and imaging systems. For the optical acoustic transducer 1310, the spot size of the probe laser determines the effective element size and then the spatial resolution.

Figure 15A:
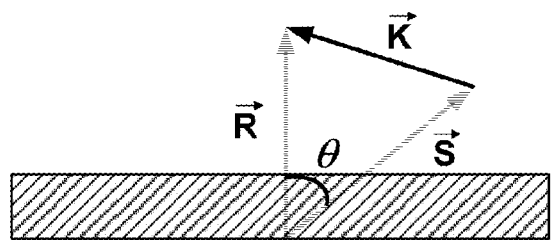
FIGS. 15A-15B are vector diagrams of a single-grating hologram (FIG. 15A) and a double-grating hologram (FIG. 15B)
Figure 15B:
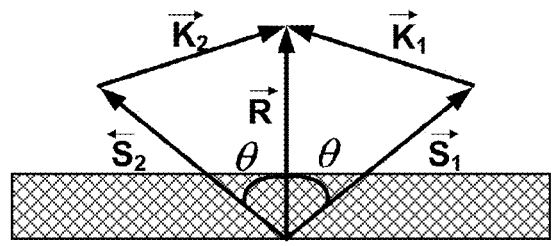

In some embodiments, the grating coupler 1312 can be a holographic grating. As FIG. 15A shows, a single-grating hologram can be designed to diffract a normal incident beam $\vec{R}$ at a specific diffraction angle θ to get a diffracted beam $\vec{S}$ by a grating vector $\vec{K}$, which can be used to form the Fabry-Pérot resonator in the defect layer 1316. Moreover, as illustrated in FIG. 15B, a double-grating hologram can be also designed to get two diffracted beams $\vec{S_1}$ and $\vec{S_2}$ from one incident beam $\vec{R}$ by the grating vectors $\vec{K_1}$ and $\vec{K_2}$ respectively, which can be used for self-referencing measurement to suppress the system noise.

Figure 15C:
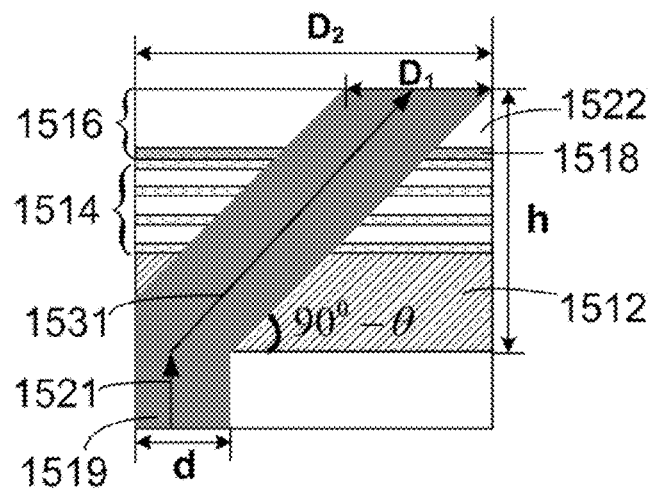
FIGS. 15C-15D are the schematic of the effective element size and transducer size of the IPC structure of FIG. 1 for an optical acoustic transducer with a single-grating hologram (FIG. 15C) and a double-grating hologram (FIG. 15D).

As FIG. 15C shows, the probe size $D_1$ is d/cos θ, where d is the diameter of the emission aperture of the input light signal 1521 from the light source 1519, and θ is the diffracted angle of the diffracted probe beam 1531 in the holographic grating 1512. The minimal transducer size $D_2$ determines the distance between two adjacent transducers thus the density of the acoustic arrays. It can be derived as: $D_2$=(h sin θ+d)/cos θ, where h is the total thickness of holographic grating 1512, the PC 1514, and the defect layer 1516 comprising the photoconductive layer 1518 and the polymer layer 1522.

Figure 15D:
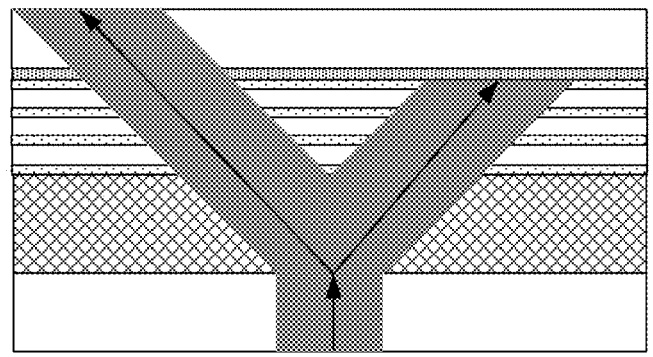

In some embodiments, the diffracted angle is 45°, and the structure thickness (including PC 1514, photoconductive layer 1518 and polymer 1522) is 6.5 μm. The holographic film 1512 can be as thin as 10 μm, and the laser aperture d is typically 5 μm. Therefore, the optical acoustic transducer 1310 can have an effective element size of 7.1 μm, and a minimal transducer size of 23.6 μm, which is one order of magnitude smaller than the existing piezoelectric transducers. Moreover, a self-referencing acoustic transducer with a double-grating hologram can be developed, as shown in FIG. 15D, where one of the probe beams is used for sensing (with polymer) and the other for reference (without polymer). It significantly decreases the noise floor, and can achieve a MDP of less than 10 dB SPL with a transducer size less than 50 μm. Such a high performance makes the optoacoustic transducer superior to any existing acoustic transducers. Moreover, the transducer size is mainly determined by the transducer configuration, and is independent of the acoustic performance (including sensitivity, frequency response, etc.), which is another big advantage compared to other piezoelectric transducers.

In some embodiments, a protective layer can be further adsorbed on top of the defect layer to protect the defect layer (in particular the polymer layer) from the moisture infiltration or humidity, or temperature fluctuation. For example, the protective layer can be a silica layer deposited on the defect layer. In addition, the optical acoustic transducer can be placed on a thermoelectric cooler (TEC) to stabilize the temperature. A suitable windscreen can be also designed to reduce environment noise and yield significant improvement onboard moving platforms.

In the following, the design, fabrication, and characterization of the optical acoustic transducer 1310 are discussed in greater detail.

In some embodiments, the optical acoustic transducer 1310 comprises four main components. The first is a surface mounted laser source 1319, providing the probe light at a desired wavelength. The second is a grating 1312, diffracting a normal incident light to a desirable angle. The third is one dimensional photonic crystal (1D PC) structure 1314. The fourth is a defect layer 1316 that comprises a photoconductive layer 1318 and an acoustic sensing layer 1322. The photoconductive layer 1318 is further designed to be a photodiode, outputting a photoconductive signal 1323.

It will be appreciated that the optical acoustic transducer 1310 can be designed to work at any desired wavelength. Any suitable light sources and photoconductive material could be chosen accordingly. In some embodiments, commercially available vertical cavity surface-emitting laser (VCSEL) with an emission wavelength at 850 nm is chosen as the laser source 1319, and Si is chosen as the photoconductive material 1318 that has a relative large responsivity at 850 nm and is compatible with standard Si processing technologies. In some embodiments, the photoconductive material 1318 can be a single layer of amorphous silicon (as illustrated in FIG. 3A) or a Si p-i-n photodiode (as illustrated in FIG. 3B).

For the design of the optical acoustic transducer 1310, a 1D PC based Si p-i-n photodiode 1610 is first designed. Different from other RCE photodiodes that work at normal incidence, the 1D PC based Si photodiode operates in a total-internal-reflection (TIR) geometry. The three Si layers (p+ implant, intrinsic, and n+ implant) need to satisfy the resonant condition in the defect layer. The intrinsic Si layer (i.e., i-Si) is also the absorbing layer in the defect layer. The i-Si layer thickness needs to be well controlled to get maximum absorption near the operating wavelength; while each Si layer thickness and implant concentrations in p+ and n+ Si layers also need to be optimized to get best performance as a photodiode. In order to achieve this goal, semiconductor simulation software such as Taurus Medici can be utilized to design the Si p-i-n photodiode, numerical simulation software such as MATLAB can be used to design the PC structure, and both of them can be accommodated to optimize the whole design.

In some embodiments, the PC based Si p-i-n photodiode 1610 is illustrated as FIG. 16A. The designed PC based Si p-i-n photodiode can fabricated on a planar substrate 1600 (e.g., BK7 glass plate). The alternating pairs of multilayers 1642 and 1644 (such as $SiN_x/SiO_2$) can be deposited using thin film coating methods (such as Plasma-enhanced chemical vapor deposition (PECVD), or low-pressure chemical vapor deposition (LPCVD), electronic beam (EB) evaporation) to form the 1D PC structure 1614, and then three polycrystalline Silicon layers 1628, 1630, and 1632 can be sequentially grown by LPCVD or molecular beam epitaxy (MBE). The p-type and n-type implanting can be accomplished by simultaneous low-energy ion implantation during the process. Finally, the electrodes 1626 can be fabricated for p and n contacts such that an output signal 1623 can be obtained as an electrical signal (such as current or voltage). The fabricated PC-based Si p-i-n photodiode 1610 can be tested in a Kretschmann-like geometry 1612 (such as a prism). Its performance including responsivity, dark current, noise floor, and frequency response, can be characterized and optimized. And a commercial Si photodiode can be used as a reference to evaluate the performance of the developed PC-based Si p-i-n photodiode.

After that, an acoustic sensor can be developed by coating a layer of acoustic sensing material like polymer on top of the PC based photodiode. FIG. 16B shows the acoustic sensor 1610', which is similar to the embodiment 1610 illustrated in FIG. 16A indicated with corresponding reference numerals by adding an apostrophe symbol ', except that the defect member 1616' comprises both the photoconductive layers 1618' and the acoustic sensing layer 1622'.

The acoustic sensing layer 1622' is designed as follows. On one hand, its refractive index and thickness should satisfy the resonant condition in the defect layer 1616', together with the designed photodiode 1618' consisting of p-i-n layers. On the other hand, suitable sensing material with suitable thickness need to be considered, as the performance of acoustic sensors mainly depends on the properties of the sensing layer, such as thickness, Young's Modulus, and acoustic impedance.

In some embodiments, PDMS can be used as the sensing polymer 1622', whose Young's modulus can vary within a wide range by adjusting the mixing ratio of the base and the curing agent of Sylgard 184 Silicone Encapsulant. The PDMS's Young modulus can be varied from 1.3 MPa (10:1) to 4 kPa (60:1). The fabricated acoustic sensor using PC based Si p-i-n photodiode and PDMS layer can be evaluated with the performance parameters including sensitivity, frequency response, noise floor, and detection range. A commercial acoustic microphone can be used as a reference.

Next, in order to miniaturize the bulky Kretschmann-like systems illustrated in FIGS. 16A-B, a specialized grating coupler can be utilized to realize compact and on-chip devices 1610" as shown in FIG. 16C. The compact acoustic sensor 1610" has a similar embodiment to 1610' as illustrated in FIG. 16B, indicated with corresponding reference numerals by changing the apostrophe symbol ' to ", except that the light coupler is a grating coupler 1612" instead of a prism coupler 1612'. The grating coupler 1612" can be designed to diffract the normal incident light 1621" at a specific angle to satisfy the requirements of the designs above. In some embodiments, the grating coupler 1612" can be a specialized holographic grating, such as single-grating hologram or double-grating hologram. The hologram can be fabricated for any suitable wavelength, such as 850 nm. It can be recorded in a photopolymer film such as DuPont photopolymer (HRF-600) film to precisely redirect input signal beams at a desired angle (e.g., 45°). The thickness of the photopolymer film can be any thickness, preferably thin thickness such as 10 μm. A Verdi laser ($\lambda$=532 nm) can be used for recording photopolymers. And the diffracted light from an 850 nm probe laser can be monitored to measure the dynamic diffraction efficiency and diffracted angle.

Thus, a compact, integrated acoustic sensor 1610" can be developed by vertically integrating all of the holographic grating 1612", the PC structure 1614", the Si photodiode 1618", and the sensing layer 1622" on the same substrate 1600", as illustrated in FIG. 16C. In some embodiments, the substrate 1600" can be a planar substrate such as BK7 glass plate, or a flexible substrate such as Kapton or PET. Preferable fabrication procedures are shown as follows:

1) When the planar substrate is adopted, the holographic grating and PC based Si photodiode can be first integrated, whose performance as a photodiode can be tested and optimized; then the structure is further coated with a suitable PDMS layer, followed by testing, and optimizing the performance as an acoustic sensor.

2) When the flexible substrate is adopted, one can coat the flexible substrate on a rigid substrate, followed by fabrication of the whole structure, and then peel it off; or to fabricate the whole structure on a planar substrate (e.g., silicon wafer), then lift off and transfer to the flexible substrate. The final flexible, compact acoustic sensors can be tested with a normal incident light, and the acoustic performance can be characterized.

Furthermore, a fully-integrated acoustic transducer, integrating both light sources and photodetectors, is highly desirable for widespread deployment. In some embodiments, vertical-cavity surface-emitting laser (VCSEL) is a perfect match for the optical acoustic transducer 1310, because it can be vertically integrated on the substrate, same as the other transducer components. Thus, one can integrate all necessary components on a flexible substrate to form a light-weight, ultra-compact acoustic transducer with low power consumption, as illustrated in FIG. 13. Two fabrication methods can be explored. The first one is to sequentially fabricate holographic grating, PC based Si photodiode, and PDMS on VCSEL-integrated flexible substrates; the other one is to fabricate the first three components on a planar substrate, then lift off, and transfer to VCSEL-integrated flexible substrates. The final acoustic sensor can be tested with normal incident beam, and the acoustic performance can be characterized and optimized, with consideration of miniaturizing the acoustic size and thickness.

It will be appreciated that the optical acoustic transducer 1310 can be redesigned based on the experimental results to ensure that the best performance can be achieved with an optimized design.

After the successful development of a conformable ultra-compact high-resolution optoacoustic transducer on flexible substrates, an acoustic transducer array on a flexible substrate can be further developed for acoustic sensing applications. A preferable procedure is as follows: 1) Develop high density light sources on flexible substrates; 2) Develop high density acoustic array sensors on flexible substrates; 3) Develop corresponding application specific integrated circuits (ASICs) on flexible substrates; 4) Fabricate a prototype of high density acoustic transducer array, characterize its performance including sensitivity, noise floor, and frequency response, and demonstrate its capability for acoustic beamforming.

The unique configuration of the optical acoustic transducer 1310 makes it possess several distinctive advantages for acoustic detections as follows:

1) The performance is independent of the transducer size. For the existing piezoelectric transducers, suspended membranes or/and piezoelectric materials are always required to detect acoustic pressure, which restrict the element size and cause large thermal noise, narrow frequency response, and low sensitivity. In contrast, the optoacoustic transducer is a one-dimensional structure, and can use any suitable sensing material with any suitable size on the top for highly sensitive acoustic detection and discrete optical method for signal read out. Therefore, its performance is not related to the transducer size, and high performance can be achieved together with small transducer size. The optoacoustic transducer is predicted to achieve a sensitivity >1 mV/Pa, a MDP<10 dB SPL, a wide frequency response (including 20 Hz to 20 kHz), and a transducer size <50 μm in diameter and <30 μm in thickness.

2) The minimum detectable pressure (MDP) can be less than 10 dB SPL. The proposed transducer is not restricted by thermal noise as piezoelectric transducers do. Instead, its MDP is mainly determined by the noise from the photodetector (e.g., dark current) and the laser intensity fluctuation, which can be minimized by a suitable architecture.

3) The acoustic response is flat within a wide frequency range including 20 Hz to 20 kHz. The displacement due to the acoustic pressure is mainly from the thickness change of the sensitive layer (e.g., PDMS layer), thus, the frequency response is mainly dependent upon the acoustic properties of the sensing layer. The resonance frequency is far beyond 1 MHz, and has a very flat response within low frequency range, including 20 Hz to 20 kHz. Note that the frequency response is also not limited by the photodiode (the electrical-related component in the proposed transducer), which has a cut-off frequency normally higher than 100 MHz.

4) Highly integrated and completed system with low power consumption. The light source (e.g., VCSEL), the grating (e.g., holographic grating), the 1D PC structure (e.g., pairs of alternating periodic $SiN_x/SiO_2$ layers), the photodiode (e.g., Si photodiode), and the sensitive layer (e.g., PDMS), can be vertically integrated on flexible substrates. Therefore, the optoacoustic structure can be highly compact, light-weight, and contained within a small volume, which are distinctive advantages compared to other existing optical microphones that require separate light sources and photodetectors. In addition, an application specific integrated circuit (ASIC) can be built on the same substrate to contain the required current driver for the semiconductor lasers and the read-out electronics for the photodiodes. Therefore, the optoacoustic transducer integrated with all necessary components needs low power consumption, which will be highly desirable for widespread deployment.

5) Integration capability on flexible substrate and acoustic metamaterials. Since the total thickness of the proposed transducer can be less than 30 μm, it can be integrated on a flexible substrate. Its flexible property also makes it to be integrated with acoustic metamaterials.

6) Compatible with current microfabrication technologies, and can be easily fabricated to form acoustic transducer arrays. The optoacoustic transducer has a vertically-stacked multilayer structure, which can be fabricated at low cost by thin film fabrication methods, such as PECVD, LPCVD, molecular beam epitaxy (MBE), electron beam evaporation, and spin coating.

Besides the advantages mentioned above, the novel optoacoustic transducer is also robust, light weight, adjustable for different requirements, immune to electromagnetic interference, etc.

It will be appreciated that all of the aforementioned features make the optoacoustic transducer an excellent, commercially viable acoustic transducer for the next generation systems in a broad range of markets such as military, aerospace, automobile, healthcare, etc. The acoustic sensor market is expected to become a $3.1 billion market in 5 years with a compounded annual growth rate of 31.7%, from $826 million in 2011. The proposed optoacoustic transducer can realize low-cost, light-weight, ultra-compact, high-resolution acoustic transducer arrays with low power consumption on any substrates, including flexible and plastic substrates. Its immediately accessible markets are acoustic reconnaissance and surveillance, aircraft fuselage arrays, microphones, touch screen devices, imaging, communications, and sensors. Additionally, due to its hybrid configuration, the transducer can integrate different optoelectronic components, polymer materials, and micro/nanostructures in novel architectures, realizing new systems for emerging applications in photoacoustic imaging, biomedical/chemical sensors, energy harvesting and storage, and space/airborne applications. It furthers the domain of potential useful applications and revenue. These include chemical, plastics, photonics, electronics, and micro/nano manufacturing.

Exemplary System 2

Optical Ultrasound Transducer Arrays

This example is to apply the integrated photonic crystal structure 10 for optical ultrasound transducer arrays. FIG. 17 schematically shows an integrated optical ultrasound transducer (IOUT) array 1710, which comprises two-dimensional (2D) array of IOUT 1810 on a common substrate 1700 and generates three-dimensional (3D) ultrasound image 1730.

There is a strong demand for high-resolution ultrasound imaging (including pulse-echo and photoacoustic imaging) techniques to obtain comprehensive morphological and functional information of important biological or industrial samples. Currently, the unavailability of 2D high-frequency transducer arrays (>50 MHz) is a major bottleneck preventing further development of real-time, high-resolution 3D imaging applications such as imaging-guided therapy. Piezoelectric ultrasound transducers are the predominant products in the market. However, it is extremely difficult to produce 2D piezoelectric arrays operating above 20 MHz, as they would naturally suffer from increased noise in small elements, complexity of electrical interconnects, and fabrication challenges. Recent advances in microfabrication technology have enabled the development of capacitive micromachined ultrasound transducers (CMUTs). It is feasible for low frequency (<10 MHz), large element arrays (e.g., 16×16), but challenging for high frequency applications.

As a promising alternative technology, optical detection of ultrasound has been investigated and has the potential to ward off the technical issues of piezoelectric and CMUT ultrasound transducers. Optical devices, including Fabry-Pérot etalons and polymer microring resonators, have been developed. Using these, ultrahigh performance for ultrasound detections with low noise equivalent pressures (NEPs) of 20 Pa, wideband frequency response (over 90 MHz), and high imaging resolution (better than 40 µm) have been demonstrated. In order to get 2D or 3D ultrasound imaging, delay-and-sum beam-forming method is usually adopted by moving probe beam or the sensor or the detector in 1D or 2D directions to emulate or synthesize an element array or detector array. In this way, however, imaging frame rate is greatly limited. Although charge-coupled device (CCD) arrays can be used for parallel detection, they are not suitable for high-frame-rate imaging. Therefore, due to the unavailability of a large transducer element array and/or a high density photodetector array until now, no 2D optical ultrasound transducer array has been realistically developed.

However, the integrated optical ultrasound transducer (IOUT) 1810 of the present disclosure can develop a drastically novel 2D fully-integrated optical ultrasound transducer (IOUT) array for real-time, high-resolution 3D ultrasound imaging. FIG. 17 shows the schematic of the IOUT array 1710. In some embodiment, the IOUT array 1710 can have an array embodiment illustrated in FIG. 5A (preferably) or FIG. 5B. The novel transducer IOUT 1810 can have the similar embodiment to 910 illustrated in FIG. 9A, indicated with corresponding reference numerals increased by 900. The operating principle of the ultrasound transducer IOUT 1810 is similar to that of the acoustic transducer 1310, except that the IOUT 1810 works in ultrasonic range (>20 kHz) and the acoustic transducer 1310 works in sound range (<20 kHz).

In the following, the performance of the IOUT 1810, including detection sensitivity, noise floor, frequency response, and effective element size, is discussed in greater detail.

In some embodiments, the ultrasound transducer IOUT 1810 can be designed as follows: substrate/$SiN_x$/($SiO_2$/$SiN_x$)$^4$/Si/PDMS/Water. The 1D PC structure 1814 is made of 4.5 pairs of alternating 141-nm $SiN_x$ layer and 409-nm $SiO_2$ layer; the photoconductive layer 1818 is 186-nm polycrystalline Si film with 88-nm p-Si, 10-nm i-Si, and 88-nm n-Si; and the sensing layer 1822 (the addition part of the defect layer) is 1.82-µm PDMS transparent film with a Young's Modulus E of 1.3 MPa. The diffracted angle out of the light coupler 1812 (such as holographic grating) is 63°. Transfer matrix simulation shows that a resonance peak width $\Delta\lambda$res is 0.10 nm, and the shift sensitivity Bs of 0.042 nm/nm. Assuming that the photodiode has a typical responsivity of 0.3 mA/mW and that the incident laser intensity $I_0$ is 1 mW, the sensitivity $S_{max}$ of the IOUT 1810 can be 0.230 mA/kPa or 230 mV/kPa with a transimpedance gain of 1 V/mA, which is higher than that of the state-of-the-art polymer microring resonators. Moreover, the sensitivity can be further improved by easily increasing the incident laser intensity $I_0$.

The IOUT 1810's noise equivalent pressure (NEP) is mainly determined by the noise coming from the photodiode (e.g., dark current) and the incident laser intensity fluctuation. First, the PC based Si photodiode can have a dark current less than 0.1 nA, thus the NEP is 0.4 µPa<<10 Pa. Second, the laser intensity fluctuation is the dominant noise source. The laser intensity normally varies within <1% over a long time period (>1 hour). Since the ultrasound signal is a short pulse (<<1 s), a noise floor less than $10^{-3}$ can be expected, corresponding to NEP of 1.3 Pa<10 Pa. Moreover, the laser intensity fluctuation can be further suppressed down to $10^{-5}$ by temperature stabilization and self-referencing.

In some embodiments, the sensing layer can be polydimethylsiloxane (PDMS)) or polymethyl-methacrylate (PMMA). FIG. 19 shows the simulated frequency response with different thickness of PDMS (solid line) and PMMA (dash line) as the sensing layer. From 1 to 3, the PDMS layer thicknesses are 0.91, 1.82, 2.74 µm; from 1' to 3', the PMMA layer thicknesses are 1.30, 2.60, 3.90 µm. More than 100 MHz bandwidth at −6 dB can be achieved using PDMS with a layer thickness less than 2 µm.

In addition, the minimum transducer size of the IOUT 1810 is determined by the defect layer thickness dx and the incident oblique angle θx in the defect layer, that is dx tan θx. In some embodiments, dx is 2 μm, and θx is 63°, thus the minimum transducer size is 4 μm, leading to a pixel smaller than 10 μm×10 μm area in size.

The imaging spatial resolution (axial resolution and lateral resolution) is determined by the transducer's frequency bandwidth and the effective element size. With a broad bandwidth (1~100 MHz) and small element size (<10 μm), the transducer IOUT 1810 and IOUT array 1710 can achieve an axial resolution better than 12 μm and a lateral resolution better than 16 μm, which is superior to any existing ultrasound imaging systems.

The unique configuration of the IOUT 1810 vertically integrates all of the laser probe beam, optical ultrasound sensor, and photodetector on the same element, which not only miniaturizes the system but also allows easy fabrication of compact, high density 2D transducer element arrays. Moreover, small element size and spacing of each array element can be easily achieved by the standard micro/nano fabrication techniques. Meanwhile, unlike piezoelectric and CMUT transducers, where their performances are greatly restricted by the element size, the IOUT array 1710 can achieve wideband frequency response, high sensitivity, and low noise equivalence pressure (NEP) simultaneously with small element size, which further enables high resolution ultrasound imaging. Table 1 summarizes the performance comparison between the existing state-of-the-art transducers and the novel transducer IOUT array 1710. It shows that the IOUT array 1710 is superior to any existing ultrasound transducer in all the important specifications, possessing the highest potential for the development of 2D ultrasound transducer arrays for real-time, high-resolution 3D imaging.

TABLE 1

Comparison of the existing transducer technologies for ultrasound detection:

| Transducers | Piezo-electric | CMUT | Optical ultrasound transducers | | |
| --- | --- | --- | --- | --- | --- |
| | | | Fabry-Pérot | Microring | IOUT |
| Bandwidth (MHz) | 30~70 | 3~8.5 | 25~75 | 1~75 | 1~100 |
| Single element size | <55 μm × 1.5 mm | 250 μm × 250 μm | Ø = 20 μm§ | Ø = 40 μm | <10 μm × 10 μm |
| Array Elements | 1 × 256 | 16 × 16 | 1 | 1 | >64 × 64 |
| NEP (Pa) | — | 3.6 | 3.9 × 10³ | 21.4 | <10 |
| Sensitivity (mV/kPa)* | — | 0.95 | 0.04 | 66.7 | >100 |
| Lateral Resolution | 75 μm | 720 μm | 20 μm | 41 μm | ~16 μm |
| Axial Resolution | 30 μm | 350 μm | 19 μm | 21 μm | ~12 μm |
| Real-time 3D Imaging | NO | YES | NO | NO | YES |

*Sensitivity is obtained with the same transimpedance gain of 1 V/mA
§The element size here is not the real transducer size, but the laser probe spot size The IOUT array 1710 of the present disclosure involves several significant innovations: 1) PC based photodiode. Different from other resonant cavity enhanced photodiodes, where the cavity containing photoconductive layer is sandwiched between two reflective mirrors, the novel PC based photodiode allows the cavity to be present on top of the structure. Such accessibility to ambient environment not only simplifies fabrication but also improves performance and enables usability with other technologies for diverse applications. 2) Optical ultrasound transducer with integrated photodiode. In contrast to all the existing optical ultrasound transducers, where optical ultrasound sensors and photodetectors are separate devices, we creatively integrate them together in the same element using the PC based photodiode and ultrasound-sensing layer, which not only simplifies the whole system but also allows the development of compact, high density transducer arrays. 3) Grating coupling for integrated PC systems. Simple but bulky Kretschmann-like configurations are usually adopted for TIR. The IOUT 1810 can use a grating to diffract a normal incident probe light at a specific angle for TIR operation, which not only allows compact devices but also enables the development of high density systems such as photodiode arrays, ultrasound transducer arrays, and biosensor arrays. 4) 2D fully-integrated optical ultrasound transducer arrays. Based on the above three innovative technologies, 2D fully-integrated optical ultrasound transducer array can be developed, which wards off all the technical issues for other optical ultrasound transducers and holds greatest potential to achieve real-time, high-resolution 3D imaging for the first time.

The design, fabrication, and characterization of the IOUT array 1710 can be similar to that described in Application Example 1. Briefly, the process includes the following steps:
1) Design and optimize the transducer structure;
2) Develop a PC based photodiode in TIR;
3) Develop ultrasound transducer using PC based photodiode and a sensing layer;
4) Develop an integrated optical ultrasound transducer using a grating, a PC based photodiode, and a sensing layer;
5) Design and construct large 2D IOUT arrays;
6) Develop application specific integrated circuits (ASICs) for 2D IOUT array operation;
7) Design and develop backend data acquisition system to process all channels in parallel;
8) Integrated all system components, and demonstrate the capability for real-time 3D imaging.

The successful development of the IOUT array 1710 can completely change current ultrasound imaging paradigm and make a significant impact on clinical diagnostics such as early stage cancer detection, cardiovascular imaging, ophthalmology, and in vivo catheter-type imaging. Moreover, a multitude of fruitful devices ranging from ultrasound transducer arrays & imaging systems, photodetectors, acoustic sensors, biosensors, pressure sensors can be developed, which have targeted markets worth over $23 billion in 2016 ($5.6 billion for ultrasound imaging, $14.4 billion for biosensors, $3.1 billion for acoustic sensors, etc.).

Exemplary System 3

IPC-based Optical Pressure Sensors

This example is to apply the integrated photonic crystal (IPC) structure 10 illustrated in FIG. 1 for optical pressure sensors, especially favorable for flexible and stretchable pressure sensors and for applications to curved surfaces. In some embodiments, the IPC-based optical pressure sensors can have the same configuration as 1010 as shown in FIG. 10.

Pressure sensors are widely adopted as input interface of various electronic devices, such as smartphone, tablet computers, display, and touch screen devices, where capacitive or resistive touch sensors are mostly adopted. A typical pressure expected for touch screen or touch threshold of a finger is ~1 kPa. Besides pressure sensing, it is also desirable to have flexible and stretchable touch sensors that are applicable to curved surfaces, making it useful towards robotics, biomedical and automobile applications. However, one challenge with stretchable electronic based pressure sensor is the limited availability of high performance stretchable conductors and semiconductors needed for device fabrication. Recently, optical pressure sensors have attracted attention as they are unaffected by electronic noise and demonstrate potential for large area applications. However, most of the optical pressure sensors are not stretchable, difficult to be scaled up to generate large arrays, and require complex (and often expensive) optical measurement tools for data collection.

However, the IPC structure described in the present disclosure, provides unique advantages to be flexible, stretchable optical pressure sensors. The IPC-based optical pressure sensor has a similar operating principle as acoustic/ultrasonic transducers exemplified in Application Examples 1 and 2. Therefore, the IPC-based optical pressure sensor can have a similar structure as those acoustic transducers and ultrasonic transducers, as well as their performance. Suppose the IPC-based optical pressure sensor has the same structure as that designed in Application Example 2, and it can have a pressure sensitivity better than 10 Pa. With a small element size 10 μm×10 μm, the weight sensitivity can be less than 10 μg. Such high performance is superior to any existing pressure sensors. In addition, the IPC-based optical pressure sensor can be fabricated on a flexible substrate such as Kapton or PEF (as described in Application Example 1), which makes it stretchable. Moreover, without the requirements of external photodetectors, the IPC-based optical pressure sensor can greatly simplify the system. Furthermore, the IPC-based optical pressure sensor can be easily fabricated into arrays with standard micro/nanofabrication technologies. In all, the IPC-based optical pressure sensor has great potential to be explored for touch screen based devices on curved surfaces, and for robotics, biomedical and automobile applications.

Exemplary System 4

Photodetector Integrated Photonic Crystal Sensors

This example is to apply the integrated photonic crystal structure 10 illustrated in FIG. 1 for photodetector integrated photonic crystal (PIPC) sensors for label-free biomolecular detections. In some embodiments, the PIPC biosensor can have the same configuration as 1110 as shown in FIG. 11.

The rapid development of analytical equipment for characterizing molecular interactions has been driven over the last two decades by the increasing demand for a better understanding of the specific interactions among biomolecules, which provide insights into fundamental biological processes and serve as the cornerstones of life science research, pharmaceutical discovery, medical diagnosis, food/water safety assurance, environmental monitoring, and homeland security. The optical label free biosensor has recently been under intensive investigation, as it is capable of detecting analytes in their natural forms without tedious and costly labeling processes and the detection can potentially be quick and of low cost while using small sample volumes. This type of biosensor usually measures the surface density of the analytes captured by the recognition molecules immobilized on the sensor surface. While a number of optical label-free sensing technologies, including interferometry, surface plasmon resonance (SPR) sensing, waveguides, ring resonators, and photonic crystals, have been developed in many applications such as detection of cancer biomarkers in serum, virus, bacteria, antibody binding, monitoring of the cell secretion, proteomics, and drug discovery, unfortunately nearly all of them suffer from the detection limit bottleneck on the order 1-10 $pg/mm^2$, which significantly hinders their utilities in applications that require an even lower detection limit (i.e., lower analyte concentrations or smaller molecules).

Sensitivity and detection limit are two important parameters to use in characterizing the performance of the optical sensors. The sensitivity S can be characterized in a number of ways, depending on the applications and detection methods, including surface binding sensitivity (nm/nm), bulk solvent refractive index sensitivity (BRIS) (nm/RIU). However, an important and inherent comparative parameter of sensing devices is the figure of merit (FOM):

$$FOM = S/\Delta\lambda$$

where $\Delta\lambda$ is the full-width of the resonant width at half-maximum (FWHM) of the optical resonator.

Sensitivity refers to the magnitude of a sensor's response to a given change in analytes on the sensor surface, and detection limit (or resolution) refers to the smallest change in analytes that can be measured. To determine the resolution of a sensor, one must characterize the noise of the sensor a. Then the smallest measurable change of the sensor is the detection limit (DL), with the expression written as:

$$DL = \sigma/S$$

Similarly, the detection limit can be specified in different ways according to the measurable changes on the sensor surface, including thickness nm, refractive index unit (RIU), surface mass density ($pg/mm^2$), concentration (pg/mL, nM), etc. Among them, the surface mass density is an especially critical performance criterion for detection of analytes present at low concentration or detection of adsorbed molecules with low molecular weight.

The following table lists the comparison of the performance of the existing commercial optical biosensors.

TABLE 2

Performance comparison of existing commercial optical biosensors

| Company | Technology | FWHM (nm) | Surface (nm/nm) | FOM* | DL ($pg/mm^2$) | Multiplexing |
|---|---|---|---|---|---|---|
| GE (Biacore) | SPR | ~60 | ~6 | 0.1 | 1 | 16 |
| Fortebio (Octet) | Bi-layer Interferometry | >100 | ~1 | <0.01 | 1 | 96, 384 |
| SRU Bio (BIND) | Resonant grating | ~1.8 | 0.5 | 0.28 | 0.1 | 96, 384, 1536 |
| Genalyte | Silicon ring resonator | 0.04 | 0.02 | 0.5 | 1 | 24 |

*FOM is defined as the ratio between surface sensitivity and FWHM

In some embodiments, the PIPC biosensor (illustrated as 1110 in FIG. 11) can be designed to operate around the wavelength of 735 nm with a structure as follows: substrate/ $TiO_2/(SiO_2/TiO_2)^3$/a-Si/$SiO_2$/water. The 1D PC structure 1114 is made of 3.5 pairs of alternating 102-nm $TiO_2$ layer and 343-nm $SiO_2$ layer; the defect layer 1116 is comprising a 30-nm amorphous Si layer 1118 and a 378-nm $SiO_2$ layer on the top. The diffracted angle out of the light coupler 1112 is 63°, and the input light signal 1121 is s-polarization light. The whole structure can be fabricated using the technologies compatible with standard complementary metal oxide semiconductor processing, such as PECVD, electronic beam evaporation, plasma etching, and sputtering, which projects significant cost reduction for mass production.

FIG. 20A shows the simulated absorption spectra of the PIPC biosensor using transfer matrix simulation, where lines 1 and 2 represent the original spectrum and the shifted spectrum (with 0.1-nm biomolecular layer adsorption). The absorption peak has a resonance wavelength around 735 nm, with a resonance width (FWHM: 0.15 nm) and 100% absorption at resonance. The surface shift sensitivity is 1.16 nm/nm, and the BRIS sensitivity is 2600 nm/RIU. Thus the FOM (surface sensitivity per FWHM) is 7.7, one or two orders of magnitude higher than the existing commercial optical biosensors.

Compared to measurement of resonance spectra shift, for a narrow resonance mode, much higher detection sensitivity can be obtained by performing an intensity measurement with a single-wavelength laser probe tuned to the steepest fall-off region of the resonance. Because of the relative large slope of the fall-off, a minor shift of the resonance mode due to the analyte's binding on the sensing surface can be transformed into a detectable change in the absorbed light intensity in the photoconductive layer Si, further outputting a detectable photocurrent change. As shown in FIG. 20B, the analyte binding event can be monitored by measuring the output photocurrent, where the analyte is starting to adsorb onto the sensing surface at time $t_0$.

Referring to the application example 1 discussed above, the overall detection sensitivity S of the PIPIC biosensor depends on three factors: the conversion efficiency of biomolecular layer thickness change or the refractive index change of the ambient medium to the resonant wavelength shift (shift sensitivity B), the conversion efficiency of resonant wavelength shift to the absorbed intensity change (optical sensitivity $O_s$), and the conversion efficiency of absorbed intensity change to the output photocurrent change (photodetector responsivity Rs). Assuming the integrated Si photodetector in the PIPC biosensor has a similar responsivity of 0.3 A/W as other resonance cavity enhanced (RCE) Si photodetectors and that the incident laser intensity $I_0$ is 1 mW, the sensitivity $S_{max}$ of the PIPC biosensor can be calculated to be: 2.86 mA/nm or 6.76 A/RIU.

Similarly, the detection limit of the PIPC biosensor is mainly determined by the noise coming from the photodetector (e.g., dark current) and the incident laser intensity fluctuation. First, the PIPC biosensor can have a dark current less than 0.1 nA, thus the detection limit can be better than 3.5× $10^{-8}$ nm or $1.5 \times 10^{-11}$ RIU. Second, the laser intensity fluctuation is the dominant noise source. The laser intensity fluctuation can be further suppressed down to $10^{-5}$ by temperature stabilization and self-referencing, and thus the detection limit can be $4.4 \times 10^{-10}$ RIU or $1.0 \times 10^{-6}$ nm, which is also corresponding to a surface mass density 1.2 fg/mm$^2$ for normal biological substances with a density of 1.2 g/cm$^3$. This performance surpasses the state-of-the-art optical biosensors (as shown in Table 2), possessing the great potential for ultrasensitive biomolecular detection.

As discussed in Application example 2, the PIPC biosensor can have a small element size less than 10 µm. Reference sensor elements adjacent the signal elements can be used for control during detection. Due to its vertically-stacked multilayer, a large-element biosensor array (e.g., 96, 384, or 1536) can be easily fabricated by the standard micro/nanofabrication technologies, for highly-multiplexing detection. Moreover, the PIPC biosensor with integrated photodetector, eliminating the requirements of light-out coupler and external photodetectors, can greatly miniaturize the whole detection system and enable highly-multiplexing detections. Furthermore, microfluidic channels can be assembled on top of the biosensor array to enable real-time measurements for kinetics, affinity, concentration analysis in biological/chemical detections. In all, the photodetector integrated photonic crystal biosensor disclosed here, is promising as next-generation sensing platform for biological research, disease diagnostics, and drug discovery.

Exemplary System 5

IPC-Based Graphene Photodetectors

This example is to apply the integrated photonic crystal (IPC) embodiment 10 illustrated in FIG. 1 for photonic crystal enhanced graphene photodetectors and their applications for sensors.

Graphene, an atomic monolayer formed by carbon hexagons, has extraordinary electronic and optical properties and holds great promise for applications in photonics and optoelectronics, including high-speed photodetectors, optical modulators, plasmonic devices, ultrafast lasers, and biological/chemical sensors, where a strong light-matter interaction is desired. Several approaches have been pursued to increase the interaction length of light with graphene and enhance the optical absorption, including combining graphene with plasmonic nanostructures or nanoparticles, quantum dots, and resonant microcavity. Among them, resonant cavity enhanced (RCE) graphene photodetectors have attracted great attention recently, where a graphene sheet is placed inside a Fabry-Pérot (FP) resonant cavity consisting of two one-dimensional photonic crystal (1D PC) structures as high-reflectivity mirrors. It benefits from a large increase of the optical field inside a resonant cavity at a design wavelength, giving rise to increase absorption thus quantum efficiency. However, as the graphene is sandwiched by the two 1D PC structures, it is prohibited from external influences, which greatly restricts its applications.

In contrast, the IPC structure described in the present disclosure provides many unique advantages for making IPC-based graphene photodetectors. On the one hand, the IPC structure can be designed to get 100% light absorption in the photoconductive material (i.e., graphene) for high quantum efficiency; on the other hand, compared to other RCE graphene photodetectors, the IPC structure provides an open operative surface on the top of the structure, accessible for external influences, which can be developed for diverse applications such as sensors. Moreover, the IPC-based graphene photodetectors simplify the whole structure by using only one 1D PC structure as reflectivity mirrors, together with a total-internal-reflection (TIR) interface. In addition, the enhancement effects (including the quantum efficiency, light absorption, and field enhancement) occur only at the design wavelength, whereas off-resonance wavelengths are rejected by the FP cavity, making these devices promising for wavelength division multiplexing systems and high signal-to-noise ratio detection systems. Due to broad absorption range of graphene, the photodetector can be designed to any desired wavelength.

In some embodiments, the IPC-based graphene photodetector can be designed to operate around the wavelength of 633 nm with a structure as follows: substrate/TiO$_2$/(SiO$_2$/TiO$_2$)$^8$/SiO$_2$/graphene/water. The 1D PC structure 14 is made of 8.5 pairs of alternating 90-nm TiO$_2$ layer and 300-nm SiO$_2$ layer; the defect layer 16 is comprising a 366-nm SiO$_2$ layer and a graphene monolayer 18 on the top. The diffracted angle out of the light coupler 12 is 63°, and the input light signal 21 is p-polarization light. The photonic crystal structure can be fabricated using the technologies compatible with standard complementary metal oxide semiconductor processing. Graphene can be one of three major kinds of graphene materials: pristine graphene prepared by the mechanical exfoliation method, graphene grown by CVD process (referred to as CVD-graphene), and reduced graphene oxide (rGO) obtained by the reduction of graphene oxide (GO), arising from the chemical exfoliation of graphite.

FIG. 21A shows the calculated spectral response of the IPC-based graphene device using transfer matrix simulation. In simulation, graphene is described by a complex refractive index $$n(\lambda) = 3.0 + i\left(\frac{C_1}{3}\right)\lambda,$$

where $C_1$=5.446 μm and $\lambda$ is the wavelength. Lines 1, 2, and 3 show the calculated results for absorption, reflection, and transmission, respectively. A narrow absorption peak (corresponding to photoconductivity response) is observed at the cavity resonance (633 nm wavelength), with an absorption efficiency of 100% and a resonance width of 1 nm. FIG. 21B shows the field intensity distribution in this structure. A large field enhancement is achieved in the graphene (at position d=0 μm) at the on-resonance wavelength of 633 nm (line 1), about 1000-fold higher than that at off-resonance wavelength of 650 nm (line 2), which indicates that the IPC-based graphene photodetector can get a much larger light confinement within the resonant cavity. Conventional graphene photodetector comprising a graphene monolayer without resonant cavities, normally has a photoresponsivity of 1~6 mA/W, with an absorption of 2.3% (at visible wavelength) with an intrinsic conversion efficiency of 50%. Thus, the IPC-based graphene photodetector with a high quantum efficiency of 100% is promising to achieve a photoresponsivity Rs of up to 0.6 A/W.

Besides its potential applications such as photodetectors, modulators, and lasers, the IPC-based graphene photodetector can be also explored as a biosensor to detect biomolecules adsorbed on the graphene surface or the change of the ambient medium. For the above structure, the shift sensitivity B$_s$ is calculated to be 0.57 nm/nm for biomolecular binding detection or 1270 nm per refractive index unit (RIU) for the refractive index change of the ambient medium. Referring to the application example 4 discussed above, the sensor sensitivity S$_{max}$ can be calculated to be 0.45 mA/nm or 1140 mA/RIU with an incident laser intensity of 1 mW. Similarly, the detection limit of the IPC-based graphene sensor is mainly determined by the noise coming from the photodetector (e.g., dark current) and the incident laser intensity fluctuation. First, the IPC based graphene photodiode can have a dark current less than 1 nA, thus the detection limit can be better than 2×10$^{-6}$ nm or 9×10$^{-10}$ RIU. Second, the laser intensity fluctuation is the dominant noise source. The laser intensity fluctuation can be further suppressed down to 10$^{-5}$ by temperature stabilization and self-referencing, which corresponds to a detection limit of 1.3×10$^{-5}$ nm or 6×10$^{-9}$ RIU.

Besides its extraordinary electronic and optical properties, graphene also has unique chemical and biological properties which can be functionalized to detect different substances, such as gas molecules, antibodies, proteins, cells, bacteria, virus, etc. Moreover, the high field enhancement on the graphene can be explored for surface-enhanced Raman scattering measurements or fluorescence spectroscopy.

The foregoing description of the embodiments has been provided for purposes of illustration and description. It is not intended to be exhaustive or to limit the scope of the present disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the present disclosure, and all such modifications are intended to be included within the scope of the present disclosure.

What is claimed is:

1. A device comprising:
    a photonic crystal structure;
    a defect member disposed adjacent the photonic crystal structure, the defect member including a photoconductive material, wherein the device is configured to receive an input light signal such that the input light signal is internally reflected within the photonic crystal structure and the defect member, such that the input light signal is absorbed by the photoconductive material within the defect member, and such that a property of the photoconductive material is changed to thereby output an output signal;
    a light coupler between the input light signal and the photonic crystal structure, wherein the input light signal is inputted to the photonic crystal structure via the light coupler; and
    a substrate, wherein the light coupler is interposed between the substrate and the photonic crystal structure, and the substrate is one of a flexible substrate, a semi-rigid substrate, and a rigid substrate.

2. The device of claim 1, further comprising a light source that provides the input light signal, wherein the light source is interposed between the substrate and the light coupler.

3. The device of claim 1, wherein a change of the input light signal is determined by measuring the change of the output signal, and the change of the input light signal includes one or more of an intensity change, a wavelength change, and a polarization change.

4. The device of claim 1, wherein the photoconductive material includes at least one of silicon, germanium, InGaAs, PbS, PbSe, GaAs, or graphene.

5. The device of claim 1, wherein the property of the photoconductive material includes electrical conductivity, and the output signal includes at least one of a current, a resistance, or a voltage.

6. The device of claim 1, wherein the defect member defines an exposed operative surface and the output signal is associated with a condition at the operative surface, and the condition at the operative surface is detected by detecting a change in the output signal.

7. The device of claim 6, wherein the exposed operative surface is on one side of the defect member opposite to the photonic crystal structure so as to be exposed to an external influence that alters the condition at the operative surface.

8. The device of claim 7, wherein the external influence that affects the condition at the operative surface is determined by measuring the output signal.

9. The device of claim 7, wherein the external influence includes at least one of an acoustic input, an ultrasound input, a pressure input, a change of ambient medium, or material adsorbed on the operative surface.

10. The device of claim 1, wherein a thickness of the defect member is determined by a resonant condition in the defect member.

11. The device of claim 1, wherein the light coupler is configured to change an incident angle of the input light signal such that the input light signal is internally reflected within the photonic crystal structure and the defect member, and the light coupler includes at least one of a grating, a reflector, or a prism.

12. The device of claim 1 configured to be at least one of a photodetector, a photoresistor, an acoustic sensor, an ultrasonic sensor, a pressure sensor, or a biosensor.

13. The device of claim 1, wherein the photoconductive material is an active gain medium, and the output signal is an excited laser signal.

14. A method comprising:
providing a photoconductive material incorporated in a defect member disposed adjacent a photonic crystal structure; and
emitting an input light signal to the photonic crystal structure via a light coupler such that the input light signal is internally reflected within the photonic crystal structure and the defect member, such that the input light signal is absorbed by the photoconductive material in the defect member, and such that a property of the photoconductive material is changed to thereby output an output signal, wherein the light coupler is between the input light signal and the photonic crystal structure and the input light signal is inputted to the photonic crystal structure via the light coupler, and wherein the light coupler is interposed between a substrate and the photonic crystal structure, and the substrate is one of a flexible substrate, a semi-rigid substrate, and a rigid substrate.

15. The method of claim 14, further comprising providing an exposed operative surface defined by the defect member, and further comprising detecting the output signal to thereby detect an external influence on the operative surface.

16. The method of claim 14, further comprising:
providing an elastic material incorporated in the defect member; and
detecting the output signal to thereby detect flexure of the elastic material due to the external influence, the external influence including at least one of a pressure input, an acoustic input, and an ultrasonic input.

17. The method of claim 14, further comprising:
providing a dielectric material incorporated in the defect member; and
detecting the output signal to thereby detect the external influence, the external influence including at least one of material adsorbed on the operative surface or a change of ambient medium on the operative surface.

18. A system comprising a plurality of devices, each of the devices comprising:
a photonic crystal structure;
a defect member disposed adjacent the photonic crystal structure, the defect member including a photoconductive material, wherein the device is configured to receive the input light signal such that the input light signal is internally reflected within the photonic crystal structure and the defect member, such that the input light signal is absorbed by the photoconductive material within the defect member, and such that a property of the photoconductive material is changed to thereby output an output signal;
a light coupler between the input light signal and the photonic crystal structure, wherein the input light signal is inputted to the photonic crystal structure via the light coupler; and
a substrate, wherein the light coupler is interposed between the substrate and the photonic crystal structure, and the substrate is one of a flexible substrate, a semi-rigid substrate, and a rigid substrate.

19. The system of claim 18, further comprising:
application specific integrated circuits coupled to the plurality of devices, the application specific integrated circuits being configured to receive output signals from the plurality of devices; and
data acquisition and analysis systems coupled to the application specific integrated circuits, the data acquisition and analysis system being configured to process the output signals.

20. The system of claim 18, wherein the plurality of devices are configured into arrays to thereby operate as a multiplexing system, the multiplexing system being one of a photodetector array, an acoustic sensor array, an ultrasonic sensor array, a pressure sensor array, and a biosensor array.

* * * * *